United States Patent
Wang et al.

(10) Patent No.: US 9,447,115 B2
(45) Date of Patent: Sep. 20, 2016

(54) ORGANIC DYES, PROCESS FOR PRODUCING THE SAME AND USE THEREOF

(71) Applicant: Changchun Institute of Applied Chemistry Chinese Academy of Sciences, Changchun (CN)

(72) Inventors: Peng Wang, Changchun (CN); Zhaoyang Yao, Changchun (CN)

(73) Assignee: Changchun Institute of Applied Chemistry Chinese Academy of Sciences, Changchun (CN)

( * ) Notice: Subject to any disclaimer, the term of this patent is extended or adjusted under 35 U.S.C. 154(b) by 0 days.

(21) Appl. No.: 14/883,160

(22) Filed: Oct. 14, 2015

(65) Prior Publication Data

US 2016/0211084 A1    Jul. 21, 2016

(30) Foreign Application Priority Data

Jan. 20, 2015 (CN) .......................... 2015 1 0028219

(51) Int. Cl.
| | |
|---|---|
| *C07D 495/06* | (2006.01) |
| *H01G 9/20* | (2006.01) |
| *C09B 57/00* | (2006.01) |
| *H01L 51/00* | (2006.01) |

(52) U.S. Cl.
CPC ............. *C07D 495/06* (2013.01); *C09B 57/00* (2013.01); *H01G 9/2031* (2013.01); *H01G 9/2059* (2013.01); *H01L 51/0071* (2013.01)

(58) Field of Classification Search
CPC .................................................. C07D 495/06
See application file for complete search history.

(56) References Cited

PUBLICATIONS

Yao et al. Angew Chem. Int. Ed. 2015, 54, 5994-5998.*

* cited by examiner

*Primary Examiner* — Matthew Coughlin
(74) *Attorney, Agent, or Firm* — Cesari and McKenna LLP

(57) ABSTRACT

The present invention provides an organic dye, a process for producing the same and the use thereof. The organic dye has the structure of formula (I) or formula (II). The regulation of the molecular energy levels and three-dimensional structures are achieved by ring-merging phenanthrocarbazole and an electron-rich thiophene unit as well as by selecting appropriate substituents. Thereby, when the organic dye of the present invention is applied to a dye-sensitized solar cell, the power conversion efficiency of the dye-sensitized solar cell is greatly improved. Meanwhile, the raw materials for the process according to the present invention have plenty of sources with low costs, so that a commercial production can be effected.

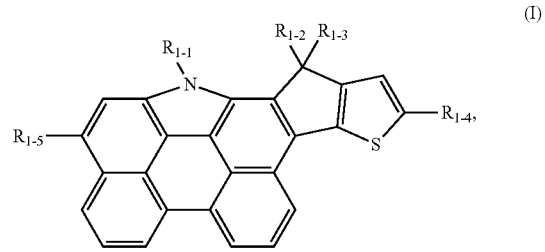

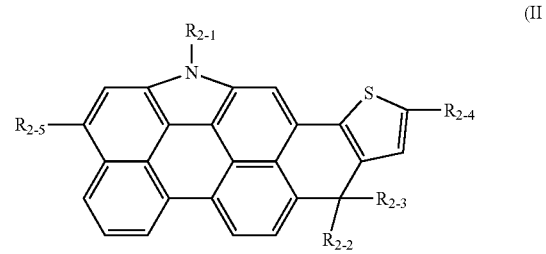

10 Claims, 2 Drawing Sheets

ORGANIC DYES, PROCESS FOR PRODUCING THE SAME AND USE THEREOF

CROSS-REFERENCE TO RELATED APPLICATIONS

This application claims the benefit of Chinese Application No. 201510028219.7 filed on Jan. 20, 2015, the content of which is hereby incorporated by reference in its entirety.

FIELD OF THE INVENTION

The present invention relates to the field of dye-sensitized solar cells, in particular, to an organic dye, a process for producing the same and the use thereof.

BACKGROUND OF THE INVENTION

The energy demand increases dramatically with the fast economic development in China. At present, China has become the largest energy-importing country in the world. Furthermore, environmental problems accompanied with consumption of the ore-based energy, such as fog and haze, are increasingly rapidly. Therefore, it is urgent to exploit the clean and sustainable energy. As a renewable and clean energy source, the development and utilization of solar energy is one of the hotspots in the field of energy study.

As an important type of solar cells, the dye-sensitized solar cell has been widely concerned all over the world. In 1991, the research group of Grätzel produced a device by adsorbing $RuL_2(\mu\text{-}(CN)Ru(CN)L'_2)_2$ (L=2,2'-bipyridyl-4,4'-dicarboxylic acid, L'=2,2'-bipyridyl), a trinuclear ruthenium dye reported by Amadelli et al as a sensitizer, on a high quality $TiO_2$ nanocrystalline film and a power conversion efficiency of 7.1% was achieved under the simulated sunlight. Therefrom, the widely research of dye-sensitized solar cell was basking in a great boom.

Dye-sensitized solar cells have lower manufacturing cost, variety of colors and good appearance compared with traditional inorganic semiconductor solar cells. Furthermore, flexible dye-sensitized solar cells are featured with their lightweight, foldable and windable abilities, and thus can be broadly used in daily life.

At present, all of the commercial available dyes are complexes containing a noble metal ruthenium. Due to its rare resource, Ruthenium-based materials are very expensive, which greatly limits the production and application thereof in large scale. Meanwhile, as another promising materials, the pure organic dyes is in full flourish despite the fact only a few devices made from pure organic dye can achieve a power conversion efficiency over 10% currently. Furthermore, the inconvenient synthesis of most of the materials used in high efficient devices also hinders the development of the pure organic dyes in dye-sensitized solar cells.

SUMMARY OF THE INVENTION

In view of above, the technical problem to be solved by the present invention is to provide an organic dye, which can be not only produced by a simple process, but also has a high power conversion efficiency.

The present invention provides an organic dye having the structure of formula (I) or (II):

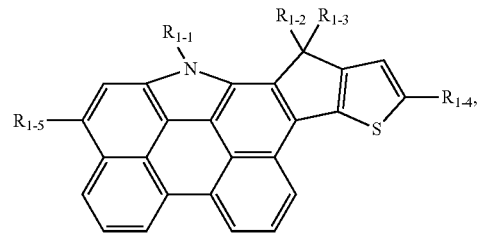

(I)

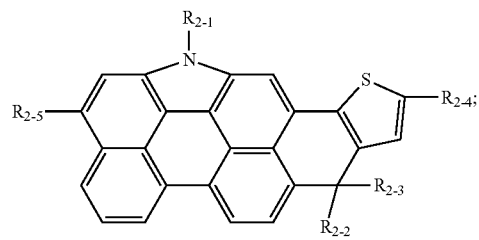

(II)

wherein $R_{1\text{-}1}$, and $R_{2\text{-}1}$ are independently selected from $C_1$-$C_{36}$ alkyl;

$R_{1\text{-}2}$, $R_{1\text{-}3}$, $R_{2\text{-}2}$, and $R_{2\text{-}3}$ are independently selected from H, $C_1$-$C_{36}$ alkyl, phenyl substituted with $C_1$-$C_{36}$ alkyl or phenyl substituted with $C_1$-$C_{36}$ alkoxy;

$R_{1\text{-}4}$, and $R_{2\text{-}4}$ are independently selected from formula (III), formula (IV), formula (V) or formula (VI):

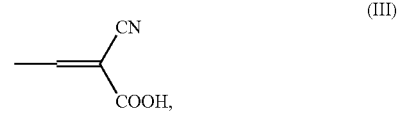

(III)

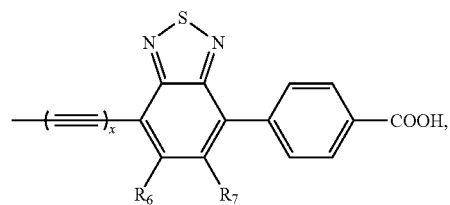

(IV)

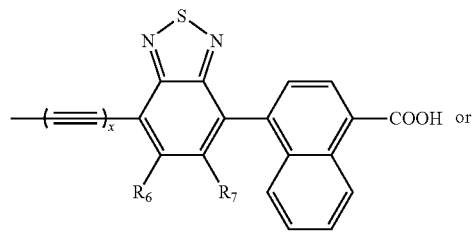

(V)

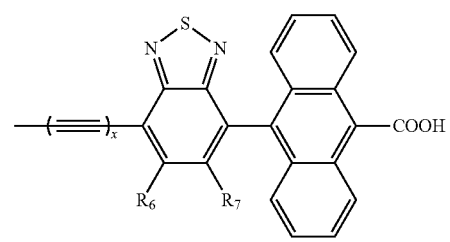

(VI)

wherein $R_6$, and $R_7$ are independently selected from H, F, $C_1$-$C_{36}$ alkyl, phenyl substituted with $C_1$-$C_{36}$ alkyl or phenyl substituted with $C_1$-$C_{36}$ alkoxy;

x is 0 or 1;

$R_{1-5}$, and $R_{2-5}$ are independently selected from hydrogen, aryl or $C_1$-$C_{36}$ alkyl.

Preferably, the aryl is aryl substituted with $C_1$-$C_{36}$ alkyl or aryl substituted with $C_1$-$C_{36}$ alkoxy.

Preferably, the aryl is selected from formula (VII), formula (VIII) or formula (IX):

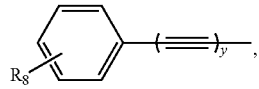

(VII)

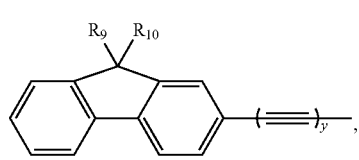

(VIII)

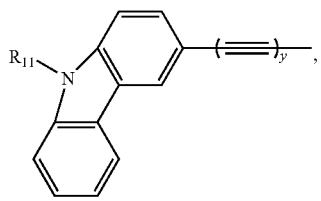

(IX)

wherein $R_8$ is H, $C_1$-$C_{36}$ alkyl or $C_1$-$C_{36}$ alkoxy;

$R_9$, $R_{10}$, and $R_{11}$ are independently selected from H or $C_1$-$C_{36}$ alkyl;

y is 0 or 1.

Preferably, said $R_{1-1}$, and $R_{2-1}$ are independently selected from $C_3$-$C_{30}$ alkyl.

Preferably, said $R_{1-2}$, $R_{1-3}$, $R_{2-2}$, and $R_{2-3}$ are independently selected from H, $C_3$-$C_{30}$ alkyl, phenyl substituted with $C_3$-$C_{30}$ alkyl or phenyl substituted with $C_3$-$C_{30}$ alkoxy.

Preferably, said organic dye has the structure of formula (X), formula (XI) or formula (XII):

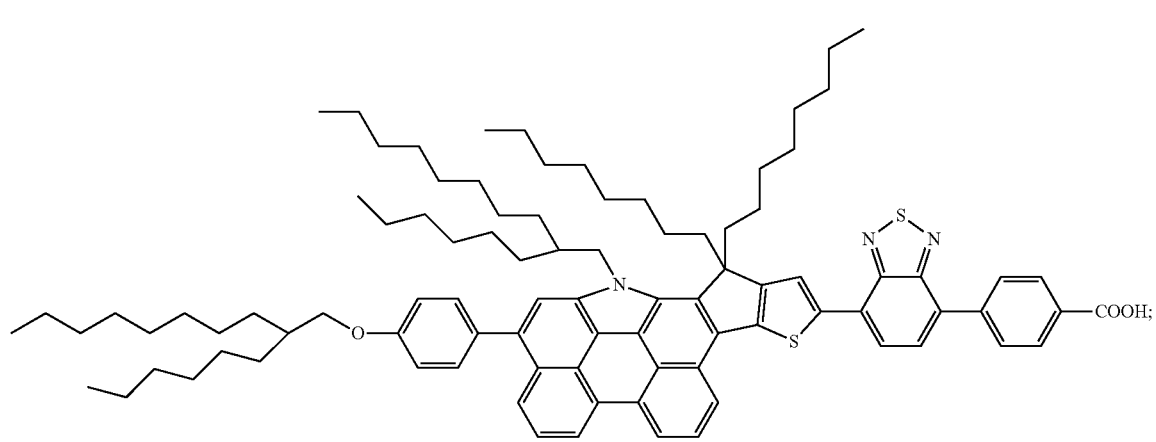

(X)

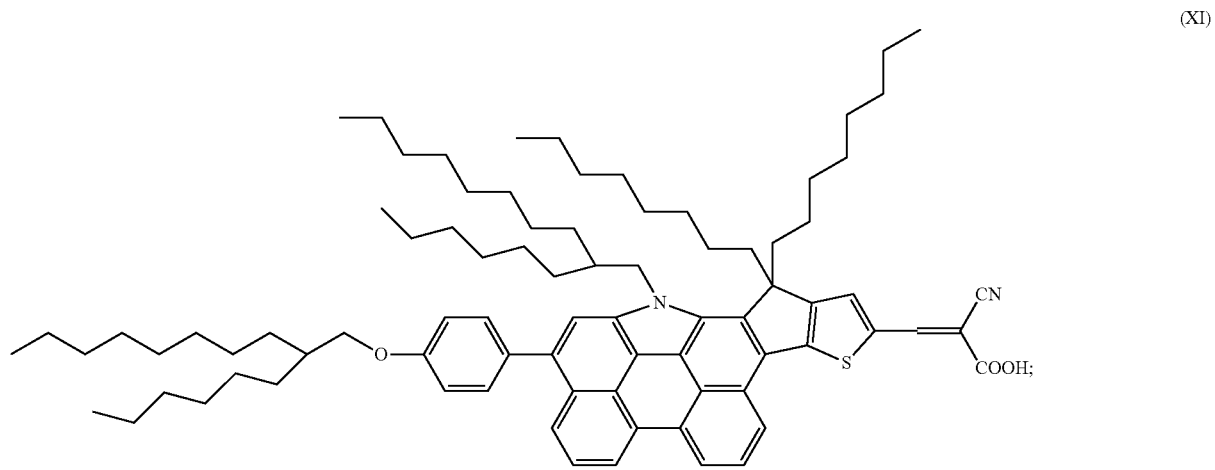

(XI)

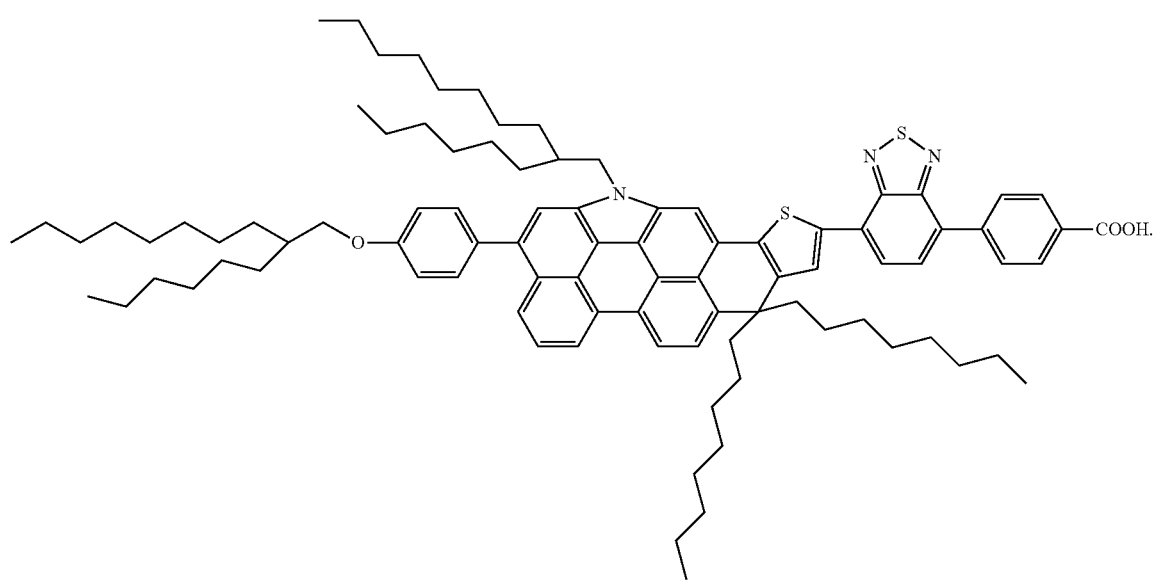

The present invention also provides a process for producing an organic dye comprising:

1) reacting a compound having the structure of formula (XIII) with a compound having the structure of formula (XIV) to give a compound having the structure of formula (XV):

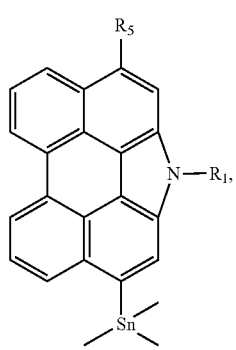

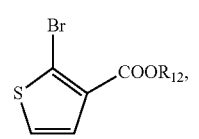

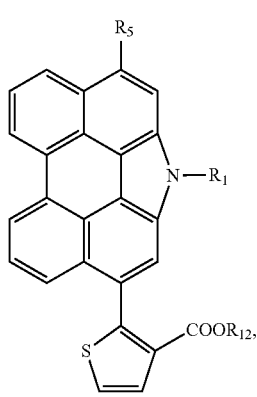

wherein $R_1$ is $C_1$-$C_{36}$ alkyl;
$R_5$ is H, aryl or $C_1$-$C_{36}$ alkyl;
$R_{12}$ is $C_1$-$C_8$ alkyl;

2) converting the compound having the structure of formula (XV) to a compound having the structure of formula (I) or formula (II):

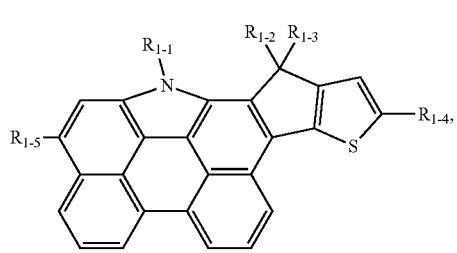

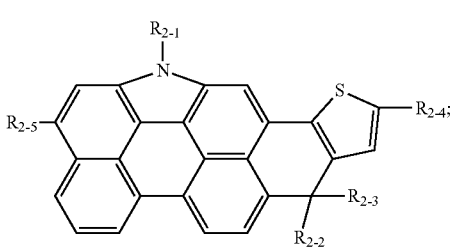

wherein $R_{1-1}$, and $R_{2-1}$ are independently selected from $C_1$-$C_{36}$ alkyl;
$R_{1-2}$, $R_{1-3}$, $R_{2-2}$, and $R_{2-3}$ are independently selected from H, $C_1$-$C_{36}$ alkyl, phenyl substituted with $C_1$-$C_{36}$ alkyl or phenyl substituted with $C_1$-$C_{36}$ alkoxy;
$R_{1-4}$, and $R_{2-4}$ are independently selected from formula (III), formula (IV), formula (V) or formula (VI):

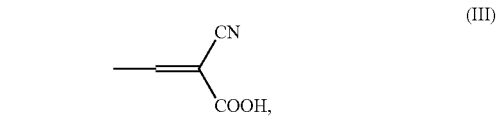

-continued

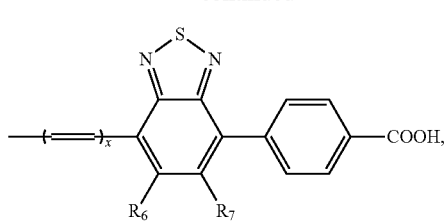
(IV)

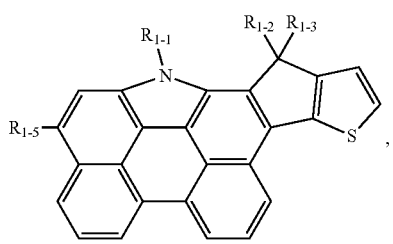
(V)

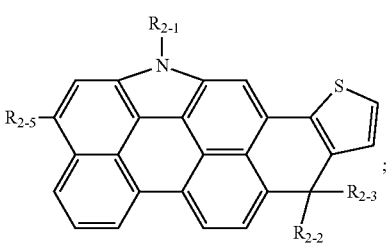
(VI)

wherein $R_6$, and $R_7$ are independently selected from H, F, $C_1$-$C_{36}$ alkyl, phenyl substituted with $C_1$-$C_{36}$ alkyl or phenyl substituted with $C_1$-$C_{36}$ alkoxy;

x is 0 or 1;

$R_{1-5}$, and $R_{2-5}$ are independently selected from H, aryl or $C_1$-$C_{36}$ alkyl.

Preferably, said step 2) specifically is as follows:

2-1) converting the compound having the structure of formula (XV) to a compound having the structure of formula (XVI) or formula (XVII):

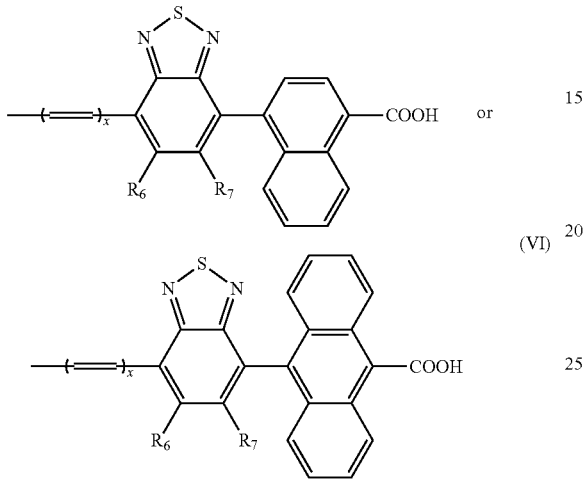

wherein $R_{1-1}$, and $R_{2-1}$ are independently selected from $C_1$-$C_{36}$ alkyl;

$R_{1-2}$, $R_{1-3}$, $R_{2-2}$, and $R_{2-3}$ are independently selected from H, $C_1$-$C_{36}$ alkyl, phenyl substituted with $C_1$-$C_{36}$ alkyl or phenyl substituted with $C_1$-$C_{36}$ alkoxy;

$R_{1-5}$, and $R_{2-5}$ are independently selected from H, aryl or $C_1$-$C_{36}$ alkyl;

2-2) reacting the compound having the structure of formula (XVI) or formula (XVII) with a compound having the structure of formula (XVIII) to give the compound having the structure of formula (I) or formula (II);

$$R_4\text{—}X \qquad (XVIII),$$

wherein $R_4$ is formula (III), formula (IV), formula (V) or formula (VI):

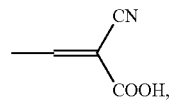
(III)

(IV)

(V)

(VI)

X is H, Br or I.

Preferably, said step 2-1) specifically is as follows:

2-1-1) converting the compound having the structure of formula (XV) into a compound having the structure of formula (XIX):

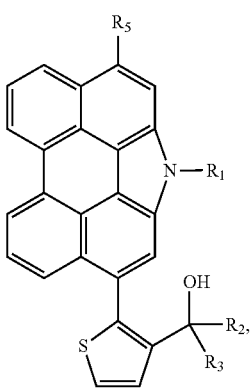
(XIX)

wherein $R_1$ is $C_1$-$C_{36}$ alkyl;

$R_2$, and $R_3$ are independently selected from H, $C_1$-$C_{36}$ alkyl, phenyl substituted with $C_1$-$C_{36}$ alkyl or phenyl substituted with $C_1$-$C_{36}$ alkoxy;

$R_5$ is H, aryl or $C_1$-$C_{36}$ alkyl.

2-1-2) converting the compound having the structure of formula (XIX) to the compound having the structure of formula (XVI) or formula (XVII).

The present invention also provides a dye-sensitized solar cell comprising an organic dye layer, wherein the organic dye layer is composed with the compound having the structure of formula (I) or formula (II) according to the present invention.

When compared with the prior art, the present invention provides an organic dye having the structure of formula (I) or formula (II), wherein the regulation and control of the molecular energy levels and three-dimensional structures are achieved by ring-merging phenanthrocarbazole and an electron-rich thiophene unit as well as by selecting appropriate substituents, thereby when the organic dye of the present invention is applied to a dye-sensitized solar cell, the power conversion efficiency of the dye-sensitized solar cell is greatly improved. As shown by the results of experiments, the power conversion efficiency of the solar cell made from the organic dye according to the present invention can be up to 11.5%.

The present invention also provides a process for producing an organic dye, wherein phenanthrocarbazole and an electron-rich thiophene unit are ring-merged by means of intramolecular cyclization, so as to achieve the conjugate extension and produce two rigid donor units. Meanwhile, the raw materials for the process of the present invention have plenty of sources with low costs, so that the industrialized production can be effected.

DETAILED DESCRIPTION OF THE INVENTION

Figure 1:
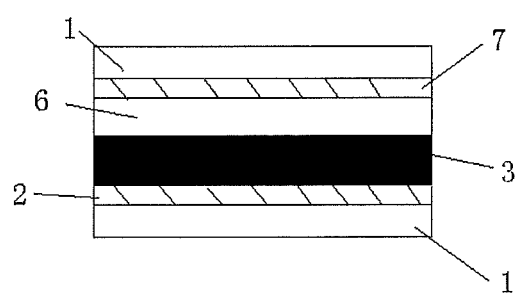
FIG. 1 is a schematic of the structure of a dye-sensitized solar cell according to the present invention.

The present invention provides an organic dye having the structure of formula (I) or formula (II):

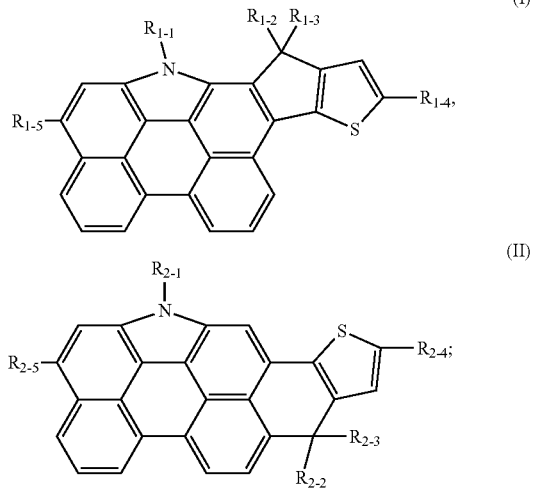

wherein $R_{1-1}$, and $R_{2-1}$ are independently selected from $C_1$-$C_{36}$ alkyl;

$R_{1-2}$, $R_{1-3}$, $R_{2-2}$, and $R_{2-3}$ are independently selected from H, $C_1$-$C_{36}$ alkyl, phenyl substituted with $C_1$-$C_{36}$ alkyl or phenyl substituted with $C_1$-$C_{36}$ alkoxy;

$R_{1-4}$, and $R_{2-4}$ are independently selected from formula (III), formula (IV), formula (V) or formula (VI):

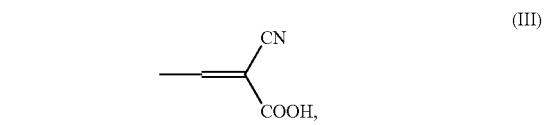

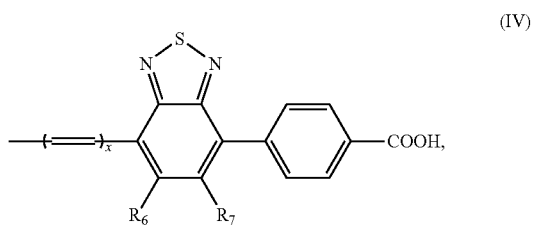

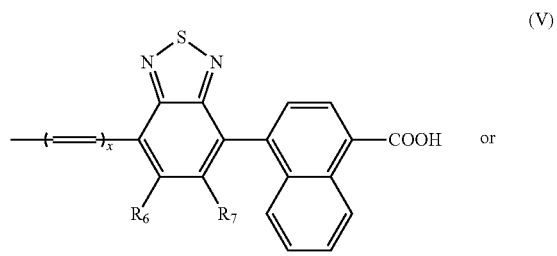

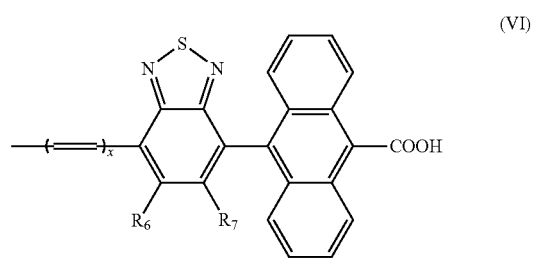

wherein $R_6$, and $R_7$ are independently selected from H, F, $C_1$-$C_{36}$ alkyl, phenyl substituted with $C_1$-$C_{36}$ alkyl or phenyl substituted with $C_1$-$C_{36}$ alkoxy;

x is 0 or 1;

$R_{1-5}$, and $R_{2-5}$ are independently selected from H, aryl or $C_1$-$C_{36}$ alkyl.

According to the present invention, said $R_{1-1}$ is preferably $C_3$-$C_{30}$ alkyl, more preferably $C_5$-$C_{26}$ alkyl, most preferably $C_{10}$-$C_{20}$ alkyl; said $R_{2-1}$ is preferably $C_3$-$C_{30}$ alkyl, more preferably $C_5$-$C_{26}$ alkyl, most preferably $C_{10}$-$C_{20}$ alkyl;

said $R_{1-2}$ is preferably $C_3$-$C_{30}$ alkyl, phenyl substituted with $C_3$-$C_{30}$ alkyl or phenyl substituted with $C_3$-$C_{30}$ alkoxy, more preferably $C_5$-$C_{26}$ alkyl, phenyl substituted with $C_5$-$C_{26}$ alkyl or phenyl substituted with $C_5$-$C_{26}$ alkoxy, most preferably $C_{10}$-$C_{20}$ alkyl, phenyl substituted with $C_{10}$-$C_{20}$ alkyl or phenyl substituted with $C_{10}$-$C_{20}$ alkoxy; said $R_{1-3}$ is preferably $C_3$-$C_{30}$ alkyl, phenyl substituted with $C_3$-$C_{30}$ alkyl or phenyl substituted with $C_3$-$C_{30}$ alkoxy, more preferably $C_5$-$C_{26}$ alkyl, phenyl substituted with $C_5$-$C_{26}$ alkyl or phenyl substituted with $C_5$-$C_{26}$ alkoxy, most preferably $C_{10}$-$C_{20}$ alkyl, phenyl substituted with $C_{10}$-$C_{20}$ alkyl or phenyl substituted with $C_{10}$-$C_{20}$ alkoxy; said $R_{2-2}$ is preferably $C_3$-$C_{30}$ alkyl, phenyl substituted with $C_3$-$C_{30}$ alkyl or phenyl substituted with $C_3$-$C_{30}$ alkoxy, more preferably $C_5$-$C_{26}$ alkyl, phenyl substituted with $C_5$-$C_{26}$ alkyl or phenyl substituted with $C_5$-$C_{26}$ alkoxy, most preferably $C_{10}$-$C_{20}$ alkyl, phenyl substituted with $C_{10}$-$C_{20}$ alkyl or phenyl substituted with $C_{10}$-$C_{20}$ alkoxy; said $R_{2-3}$ is preferably $C_3$-$C_{30}$ alkyl, phenyl substituted with $C_3$-$C_{30}$ alkyl or phenyl substituted with $C_3$-$C_{30}$ alkoxy, more preferably $C_5$-$C_{26}$ alkyl, phenyl substituted with $C_5$-$C_{26}$ alkyl or phenyl substituted with $C_5$-$C_{26}$ alkoxy, most preferably $C_{10}$-$C_{20}$ alkyl, phenyl substituted with $C_{10}$-$C_{20}$ alkyl or phenyl substituted with $C_{10}$-$C_{20}$ alkoxy.

$R_{1-5}$ is preferably $C_1$-$C_{36}$ alkyl or aryl, said alkyl is preferably $C_3$-$C_{30}$ alkyl, more preferably $C_5$-$C_{26}$ alkyl, most preferably $C_{10}$-$C_{20}$ alkyl, said aryl is preferably an unsaturated hydrocarbyl of aryl substituted with $C_1$-$C_{36}$ alkyl or an unsaturated hydrocarbyl of aryl substituted with $C_1$-$C_{36}$ alkoxy, more preferably the aryl is preferably an unsaturated hydrocarbyl of aryl substituted with $C_3$-$C_{30}$ alkyl or an unsaturated hydrocarbyl of aryl substituted with $C_3$-$C_{30}$ alkoxy, most preferably the aryl is preferably an unsaturated hydrocarbyl of aryl substituted with $C_5$-$C_{26}$ alkyl or an unsaturated hydrocarbyl of aryl substituted with $C_5$-$C_{26}$ alkoxy, still most preferably the aryl is preferably an unsaturated hydrocarbyl of aryl substituted with $C_{10}$-$C_{20}$ alkyl or an unsaturated hydrocarbyl of aryl substituted with $C_{10}$-$C_{20}$ alkoxy; particularly, the aryl is formula (VII), formula (VIII) or formula (IX),

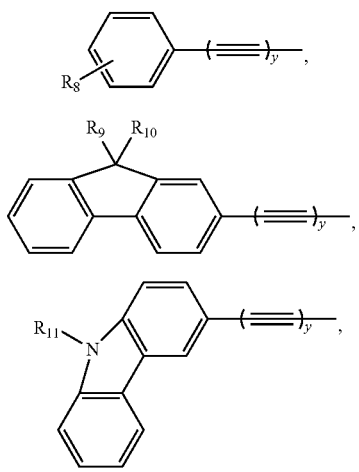

wherein $R_8$ is H, $C_1$-$C_{36}$ alkyl or $C_1$-$C_{36}$ alkoxy, preferably $C_3$-$C_{30}$ alkyl or $C_3$-$C_{30}$ alkoxy, more preferably $C_5$-$C_{26}$ alkyl or $C_5$-$C_{26}$ alkoxy, most preferably $C_{10}$-$C_{20}$ alkyl or $C_{10}$-$C_{20}$ alkoxy;

$R_9$, $R_{10}$, and $R_{11}$ are independently selected from H or $C_1$-$C_{36}$, preferably $C_3$-$C_{30}$ alkyl, more preferably $C_5$-$C_{26}$ alkyl, most preferably $C_{10}$-$C_{20}$ alkyl;

y is 0 or 1.

said $R_{2-5}$ is preferably $C_1$-$C_{36}$ alkyl or aryl, said alkyl is preferably $C_3$-$C_{30}$ alkyl, more preferably $C_5$-$C_{26}$ alkyl, most preferably $C_{10}$-$C_{20}$ alkyl, said aryl is preferably an unsaturated hydrocarbyl of aryl substituted with $C_1$-$C_{36}$ alkyl or an unsaturated hydrocarbyl of aryl substituted with $C_1$-$C_{36}$ alkoxy, more preferably the aryl is preferably an unsaturated hydrocarbyl of aryl substituted with $C_3$-$C_{30}$ alkyl or an unsaturated hydrocarbyl of aryl substituted with $C_3$-$C_{30}$ alkoxy, most preferably the aryl is preferably an unsaturated hydrocarbyl of aryl substituted with $C_5$-$C_{26}$ alkyl or an unsaturated hydrocarbyl of aryl substituted with $C_5$-$C_{26}$ alkoxy, still most preferably the aryl is preferably an unsaturated hydrocarbyl of aryl substituted with $C_{10}$-$C_{20}$ alkyl or an unsaturated hydrocarbyl of aryl substituted with $C_{10}$-$C_{20}$ alkoxy; particularly, the aryl is formula (VII), formula (VIII) or formula (IX):

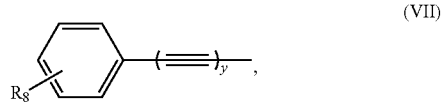

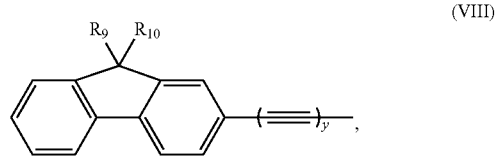

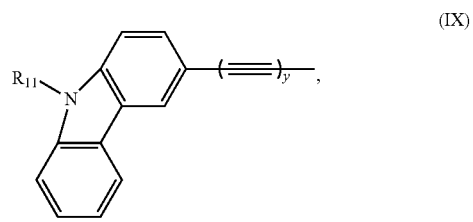

wherein $R_8$ is H, $C_1$-$C_{36}$ alkyl or $C_1$-$C_{36}$ alkoxy, preferably $C_3$-$C_{30}$ alkyl or $C_3$-$C_{30}$ alkoxy, more preferably $C_5$-$C_{26}$ alkyl or $C_5$-$C_{26}$ alkoxy, most preferably $C_{10}$-$C_{20}$ alkyl or $C_{10}$-$C_{20}$ alkoxy;

$R_9$, $R_{10}$, and $R_{11}$ are independently selected from H or $C_1$-$C_{36}$, preferably $C_3$-$C_{30}$ alkyl, more preferably $C_5$-$C_{26}$ alkyl, most preferably $C_{10}$-$C_{20}$ alkyl;

y is 0 or 1.

said $R_6$ is preferably H, $C_2$-$C_{30}$ alkyl, phenyl substituted with $C_2$-$C_{30}$ alkyl or phenyl substituted with $C_2$-$C_{30}$ alkoxy, more preferably H, $C_3$-$C_{20}$ alkyl, phenyl substituted with $C_3$-$C_{20}$ alkyl or phenyl substituted with $C_3$-$C_{20}$ alkoxy, most preferably H, $C_4$-$C_{10}$ alkyl, phenyl substituted with $C_4$-$C_{10}$ alkyl or phenyl substituted with $C_4$-$C_{10}$ alkoxy, still most preferably H, $C_5$-$C_8$ alkyl, phenyl substituted with $C_5$-$C_8$ alkyl or phenyl substituted with $C_5$-$C_8$ alkoxy; said $R_7$ is preferably H, $C_2$-$C_{30}$ alkyl, phenyl substituted with $C_2$-$C_{30}$ alkyl or phenyl substituted with $C_2$-$C_{30}$ alkoxy, more preferably H, $C_3$-$C_{20}$ alkyl, phenyl substituted with $C_3$-$C_{20}$ alkyl or phenyl substituted with $C_3$-$C_{20}$ alkoxy, most preferably H, $C_4$-$C_{10}$ alkyl, phenyl substituted with $C_4$-$C_{10}$ alkyl or phenyl substituted with $C_4$-$C_{10}$ alkoxy, still most preferably H, $C_5$-$C_8$ alkyl, phenyl substituted with $C_5$-$C_8$ alkyl or phenyl substituted with $C_5$-$C_8$ alkoxy.

Particularly, said organic dye has the structure of formula (X), formula (XI) or formula (XII):

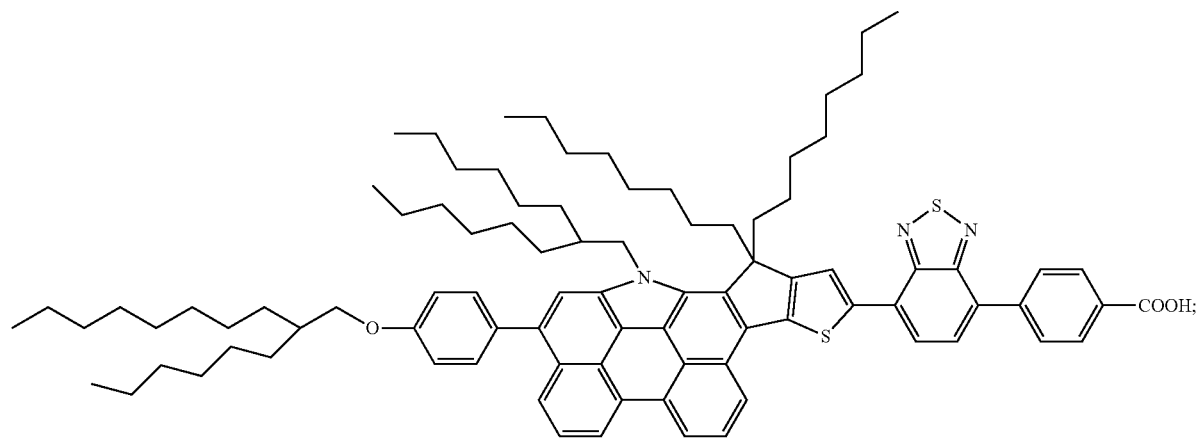
(X)
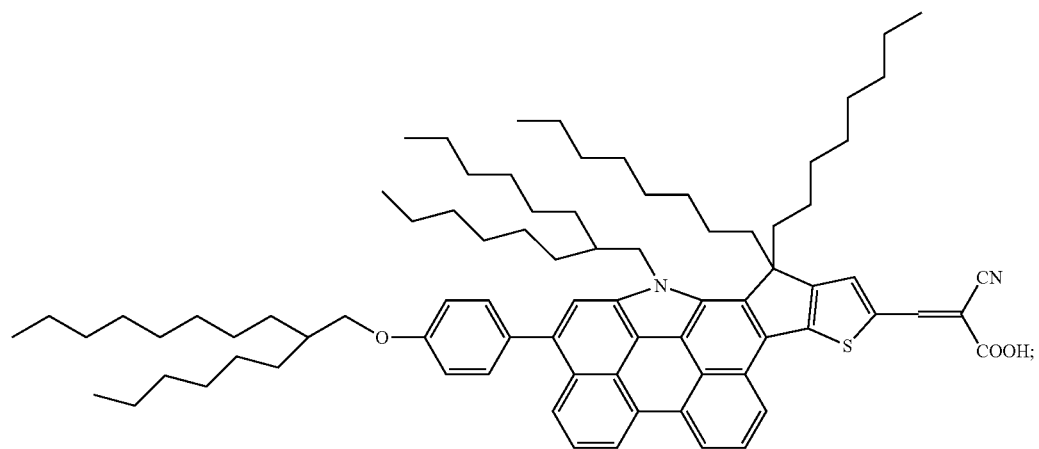
(XI)
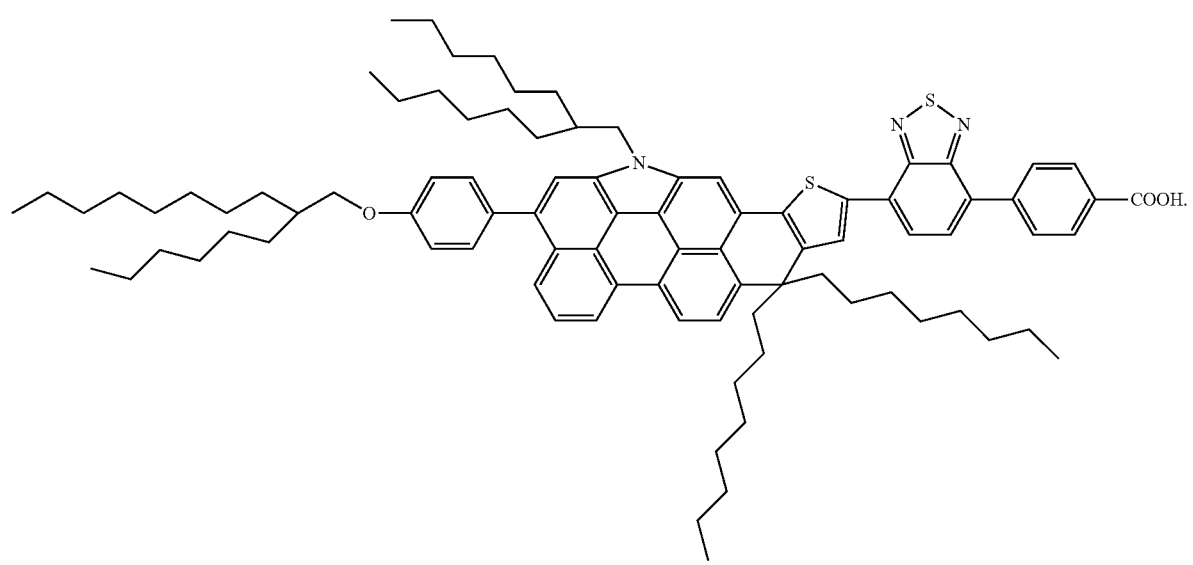
(XII)

The present invention also provides a process for producing an organic dye, comprising:

1) reacting a compound having the structure of formula (XIII) with a compound having the structure of formula (XIV) to give a compound having the structure of formula (XV)

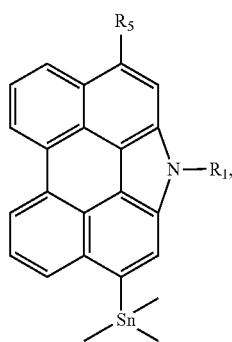
(XIII)

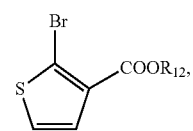
(XIV)

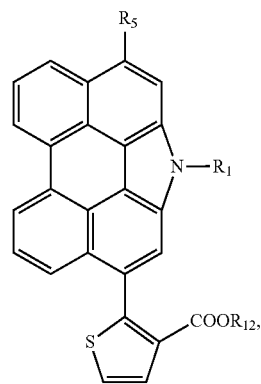
(XV)

wherein R$_1$ is C$_1$-C$_{36}$ alkyl;

R$_5$ is H, aryl or C$_1$-C$_{36}$ alkyl;

R$_{12}$ is C$_1$-C$_8$ alkyl.

2) converting the compound having the structure of formula (XV) into a compound having the structure of formula (I) or formula (II):

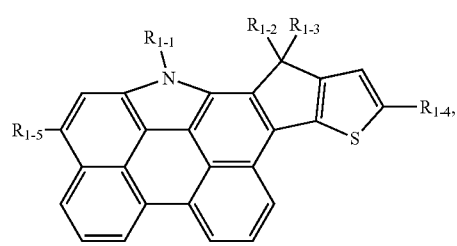
(I)

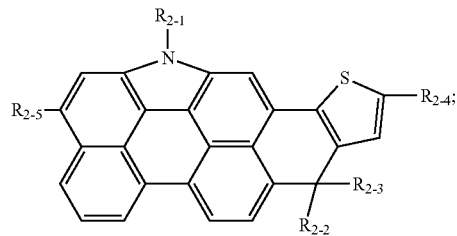
(II)

wherein R$_{1-1}$, and R$_{2-1}$ are independently selected from C$_1$-C$_{36}$ alkyl;

R$_{1-2}$, R$_{1-3}$, R$_{2-2}$, and R$_{2-3}$ are independently selected from H, C$_1$-C$_{36}$ alkyl, phenyl substituted with C$_1$-C$_{36}$ alkyl or phenyl substituted with C$_1$-C$_{36}$ alkoxy;

R$_{1-4}$, and R$_{2-4}$ are independently selected from formula (III), formula (IV), formula (V) or formula (VI):

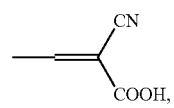
(III)

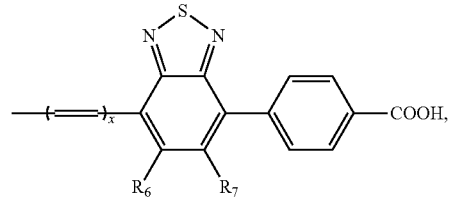
(IV)

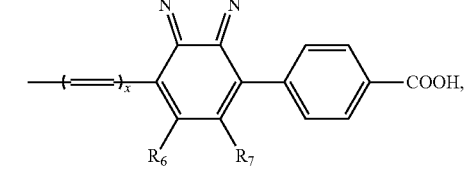
(V)

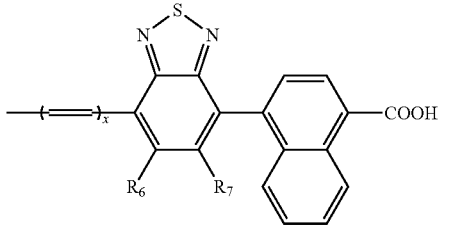
(VI)

wherein R$_6$, and R$_7$ are independently selected from H, F, C$_1$-C$_{36}$ alkyl, phenyl substituted with C$_1$-C$_{36}$ alkyl or phenyl substituted with C$_1$-C$_{36}$ alkoxy;

x is 0 or 1;

R$_{1-5}$, and R$_{2-5}$ are independently selected from hydrogen, aryl or C$_1$-C$_{36}$ alkyl.

According to the present invention, a compound having the structure of formula (XIII) is reacted with a compound having the structure of formula (XIV) to give a compound having the structure of formula (XV), wherein said R$_1$ is preferably C$_3$-C$_{30}$ alkyl, more preferably C$_5$-C$_{26}$ alkyl, most preferably C$_{10}$-C$_{20}$ alkyl; said R$_5$ is preferably C$_1$-C$_{36}$ alkyl or aryl, said alkyl is preferably C$_3$-C$_{30}$ alkyl, more preferably C$_5$-C$_{26}$ alkyl, most preferably C$_{10}$-C$_{20}$ alkyl, said aryl is preferably an unsaturated hydrocarbyl of aryl substituted with C$_1$-C$_{36}$ alkyl or an unsaturated hydrocarbyl of aryl substituted with C$_1$-C$_{36}$ alkoxy, more preferably the aryl is preferably an unsaturated hydrocarbyl of aryl substituted with C$_3$-C$_{30}$ alkyl or an unsaturated hydrocarbyl of aryl substituted with C$_3$-C$_{30}$ alkoxy, most preferably the aryl is preferably an unsaturated hydrocarbyl of aryl substituted with C$_5$-C$_{26}$ alkyl or an unsaturated hydrocarbyl of aryl substituted with C$_5$-C$_{26}$ alkoxy, still most preferably the aryl is preferably an unsaturated hydrocarbyl of aryl substituted with C$_{10}$-C$_{20}$ alkyl or an unsaturated hydrocarbyl of aryl substituted with C$_{10}$-C$_{20}$ alkoxy; particularly, the aryl is formula (VII), formula (VIII) or formula (IX); R$_{12}$ is preferably C$_2$-C$_6$ alkyl, more preferably C$_3$-C$_5$ alkyl.

Said compound having the structure of formula (XIII) is preferably produced by the following process:

reacting a compound having the structure of formula (XX) with a compound having the structure of formula (XXI) to give a compound having the structure of formula (XIII);

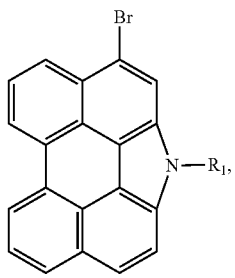

(XX), wherein the selection range of R$_1$ is ibid;

R$_5$—X (XXI), wherein the selection range of R$_5$ is ibid, X is Br—, I— or a borate ester group, preferably a borate ester group.

Particularly, the reaction catalyst is preferably Pd(OAc)$_2$ and an organic phosphine ligand, 2-bicyclohexylphosphino-2',6'-dimethoxybiphenyl (Sphos); and the reaction solvent is preferably a mixed solvent of 1,4-dioxane and water; and the reaction temperature is preferably 100 to 130° C.

In the present invention, the source of the compound having the structure of formula (XX) is not particularly limited, and preferably, it is synthesized in accordance with the method disclosed in W. Jiang, H. Qian, Y. Li, Z. Wang, *J. Org. Chem.* 2008, 73, 7369.

In order to perform the reaction better, it is preferred in the present invention to convert the compound having the structure of formula (XIII) into a compound having the structure of formula (XXII), and then react it with the compound having the structure of formula (XIV) to give the compound having the structure of formula (XV),

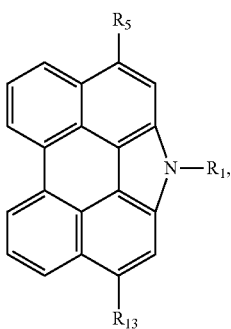

(XXII), wherein R$_{13}$ is Br—, I— or Sn(CH$_3$)$_3$—.

According to the present invention, the compound having the structure of formula (XV) is converted into the compound having the structure of formula (I) or formula (II).

Particularly, it is preferred in the present invention to convert the compound having the structure of formula (XV) into a compound having the structure of formula (XVI) or a compound having the structure of formula (XVII) firstly by Grignard's reaction and intramolecular Friedel-Crafts alkylation reaction;

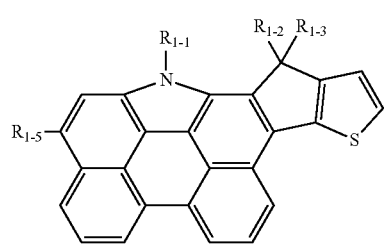

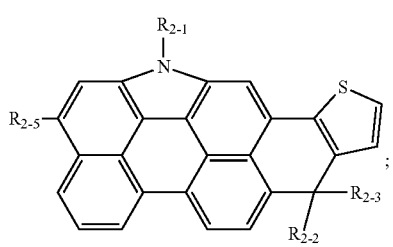

wherein R$_{1-1}$, and R$_{2-1}$ are independently selected from C$_1$-C$_{36}$ alkyl;

R$_{1-2}$, R$_{1-3}$, R$_{2-2}$, and R$_{2-3}$ are independently selected from H, C$_1$-C$_{36}$ alkyl, phenyl substituted with C$_1$-C$_{36}$ alkyl or phenyl substituted with C$_1$-C$_{36}$ alkoxy;

R$_{1-5}$, and R$_{2-5}$ are independently selected from H, aryl or C$_1$-C$_{36}$ alkyl.

More particularly, it is preferred in the present invention to convert the compound having the structure of formula (XV) into a compound having the structure of formula (XIX), and then convert the compound having the structure of formula (XIX) into the compound having the structure of formula (XVI) or formula (XVII). In particular, it is preferred in the present invention to react the compound having the structure of formula (XV) with a Grignard's reagent to give a compound having the structure of formula (XIX); and then cyclize the compound having the structure of formula (XIX) in the presence of an acid catalyst to give the compound having the structure of formula (XVI) or formula (XVII). Said acid catalyst is preferably Amberlyst 15.

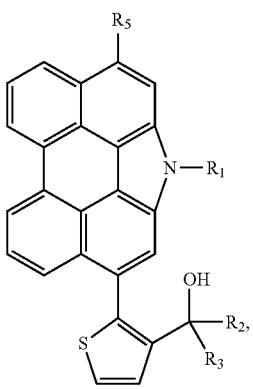

wherein R$_1$ is C$_1$-C$_{36}$ alkyl;

$R_2$, and $R_3$ are independently selected from H, $C_1$-$C_{36}$ alkyl, phenyl substituted with $C_1$-$C_{36}$ alkyl or phenyl substituted with $C_1$-$C_{36}$ alkoxy;

$R_5$ is H, aryl or $C_1$-$C_{36}$ alkyl.

According to the present invention, it is preferred in the present invention to react the compound having the structure of formula (XVI) or formula (XVII) with a compound having the structure of formula (XVIII) to give the compound having the structure of formula (I) or formula (II);

$$R_4\text{—}X_1 \quad (XVIII),$$

wherein $R_4$ is formula (III), formula (IV), formula (V) or formula (VI):

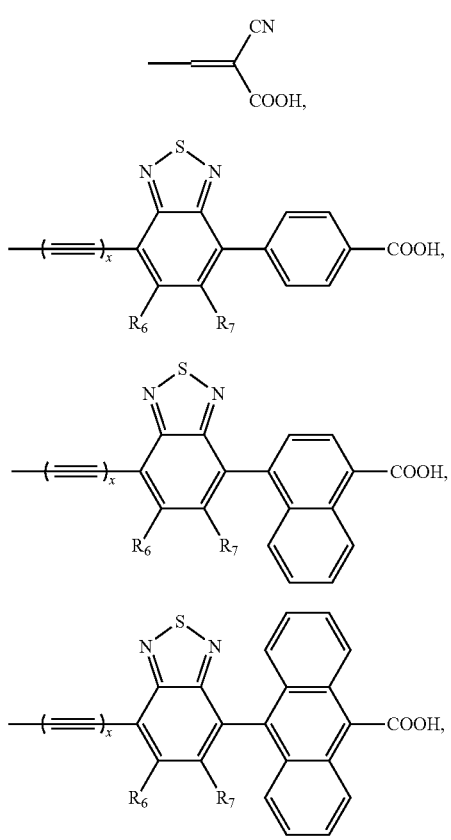

$X_1$ is H, Br or I.

In order to perform the reaction better, it is preferred in the present invention to convert the compound having the structure of formula (XVI) or the compound having the structure of formula (XVII) into a compound having the structure of formula (XXIII) or formula (XXIV),

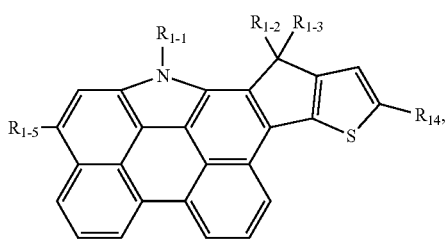

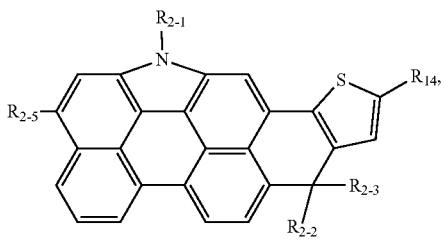

wherein $R_{14}$ is preferably a leaveable group or an aldehyde group, more preferably Br—, $Sn(CH_3)_3$— or —CHO. Then, the compound having the structure of formula (XXIII) or formula (XXIV) is reacted with the compound having the structure of formula (XVIII) to give the compound having the structure of formula (I) or formula (II). The reaction catalyst used is preferably $Pd_2(PPh_3)_2Cl_2$, $Pd_2(dba)_3$/$P(t\text{-}Bu)_3$, or $CH_3COONH_4$.

Figure 2:
FIG. 2 is a schematic of the structure of a light absorption layer in a dye-sensitized solar cell according to the present invention.

The present invention also provides a dye-sensitized solar cell, comprising an organic dye layer, which contains the compound having the structure of formula (I) or formula (II) according to the present invention. Particularly, FIGS. 1 and 2 show the structures of dye-sensitized solar cells according to the present invention, in which FIG. 1 is a schematic of the structure of a dye-sensitized solar cell according to the present invention. FIG. 2 is a schematic of the structure of a light absorption layer in a dye-sensitized solar cell according to the present invention. As seen from the figures, the dye-sensitized solar cell according to the present invention consists of transparent substrate layers 1, a conductive layer 2, a light absorption layer 3, a hole transport layer 6 and a counter electrode 7. Inside the two transparent substrate layers 1, the conductive layer 2, the light absorption layer 3, the hole transport layer 6 and the counter electrode 7 are attached successively. The light absorption layer 3 consists of a semiconductor micro/nanoparticle layer 4 and a organic dye layer 5, wherein the semiconductor micro/nanoparticle layer 4 is attached to the conductive layer 2, while the organic dye layer 5 is attached to the hole transport layer 6.

Figure 3:
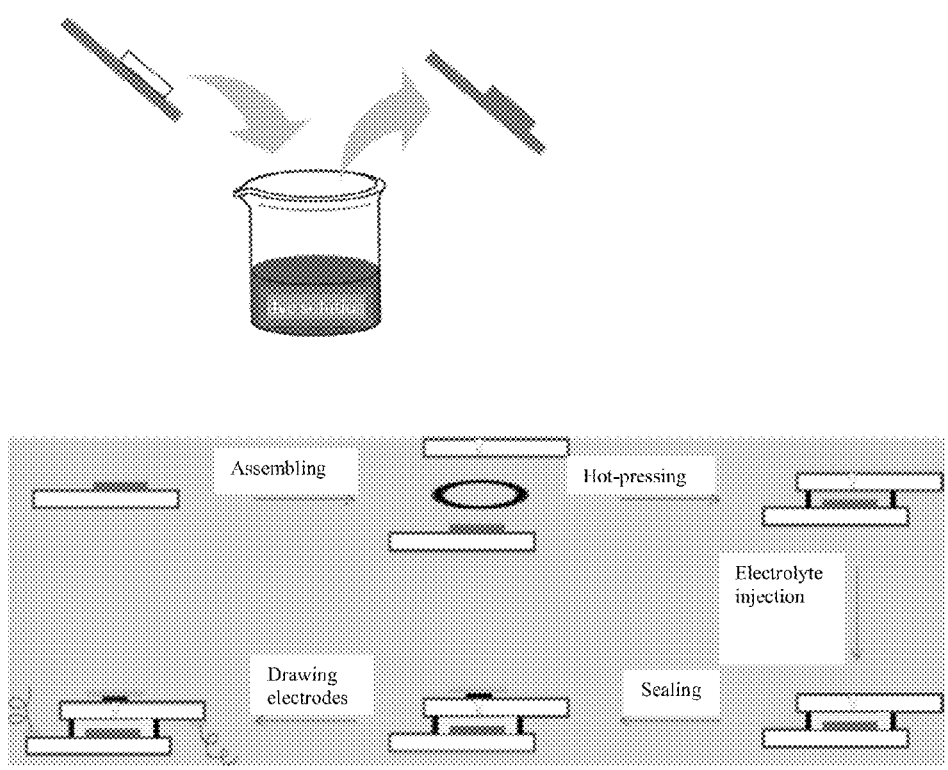
FIG. 3 is the process flow chart for the manufacture of a dye-sensitized solar cell according to the present invention.

FIG. 3 shows the manufacture process of the dye-sensitized solar cell according to the present invention. FIG. 3 is the process flow chart for the manufacture of the dye-sensitized solar cell according to the present invention.

The present invention provides an organic dye having the structure of formula (I) or formula (II), wherein the regulation and control of the molecular energy levels and three-dimensional structures are achieved by ring-merging phenanthrocarbazole and an electron-rich thiophene unit as well as by selecting appropriate substituents, thereby when the organic dye according to the present invention is applied to a dye-sensitized solar cell, the photoelectric conversion efficiency of the dye-sensitized solar cell is greatly improved.

The present invention also provides a process for producing an organic dye, in which phenanthrocarbazole and an electron-rich thiophene unit are ring-merged by means of intramolecular cyclization, so as to achieve the conjugate extension and produce two rigid donor units. Meanwhile, the raw materials for the process of the present invention have plenty of sources with low costs, so that the industrialized production can be effected.

Hereinafter, the present invention will be clearly and fully described with reference to the technical solutions of examples. Obviously, the examples described are only a part of the examples of the present invention, rather than the whole examples. All other examples, which can be obtained by those skilled in the art without any inventive work based on the examples in the present invention, fall into the protection scope of the invention.

Example 1
Scheme 1
Preparation of the compound having the structure of formula (X)
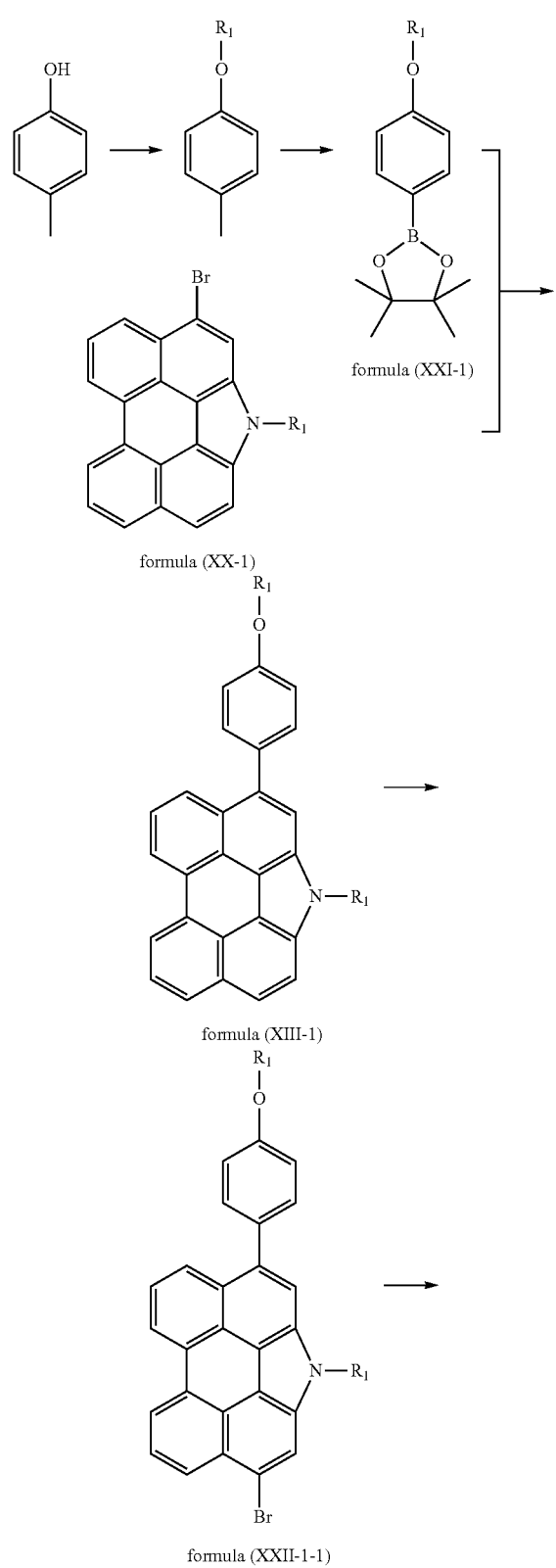
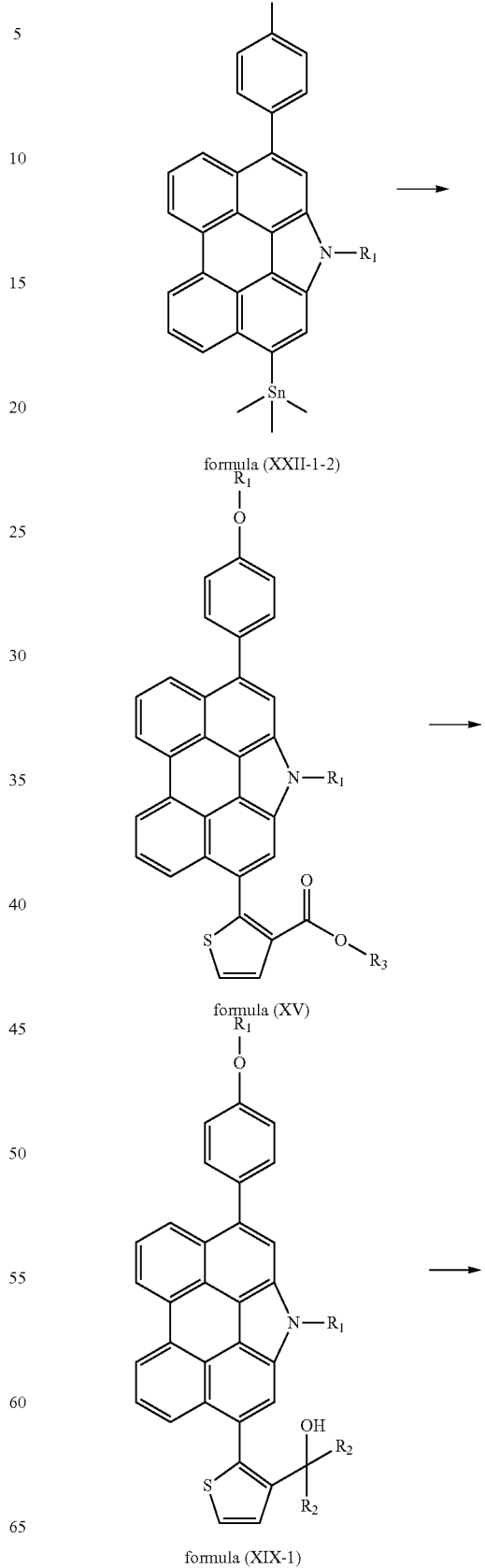

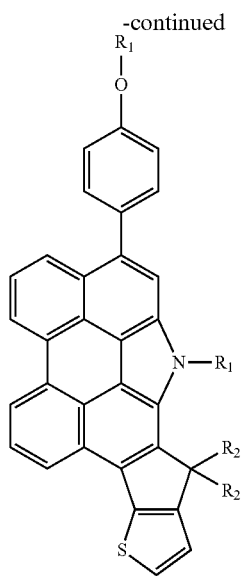
formula (XVI-1)
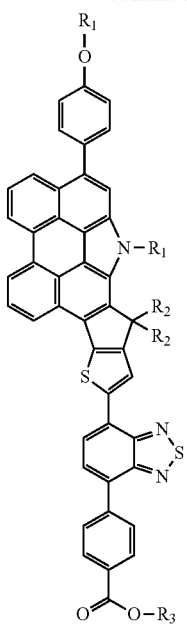
formula (X-1)
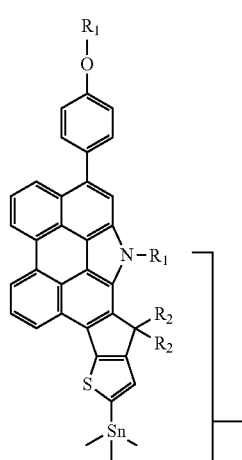
formula (XXIII-1)
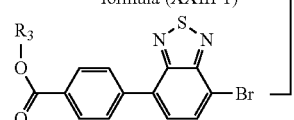
formula (XVIII-1)
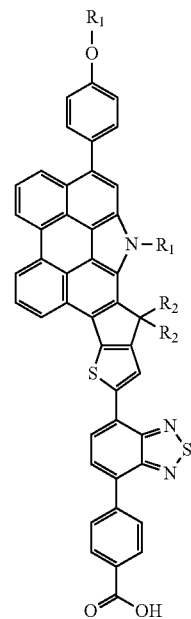
formula (X)
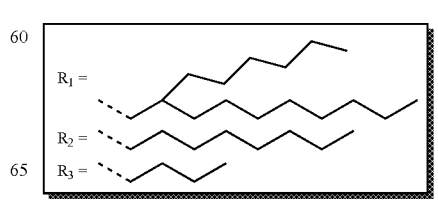

The compound having the structure of formula (XX) was synthesized in accordance with the reference document (W. Jiang, H. Qian, Y. Li, Z. Wang, *J Org. Chem.* 2008, 73, 7369). The compound having the structure of formula (XVIII) was synthesized in accordance with the reference document (Zhang, M.; Wang, Y.; Xu, M.; Ma, W.; Li, R.; Wang, P. *Energy Environ. Sci.* 2013, 6, 2944-2949). 2-bromo-3-butyl ester thiophene was purchased from J&K Scientific. The sources of other raw materials, solvents and catalysts used in the preparation process of the dye are not particularly limited, and they can be generally commercially available, or prepared in accordance with the methods well-known in the art.

Synthesis of p-2-hexyldecyloxy iodobenzene

In a three-necked round-bottom flask, p-iodophenol (2.00 g) was dissolved in 20 mL N, N-dimethyl formamide, Then 2-hexyldecyl-4-methyl benzene sulfonate (3.60 g) and potassium hydroxide (2.55 g) were added to the reaction system. The mixture was stirred overnight at 100° C.

After completion of the reaction, the mixture was extracted three times with chloroform before the organic phase was washed with water and dried over anhydrous sodium sulfate. After solvent removal under reduced pressure, the crude product was purified by column chromatography (petroleum ether 60-90° C.) on silica gel to yield p-2-hexyldecyloxy iodobenzene (4.04 g, 97% yield).

The resultant p-2-hexyldecyloxy iodobenzene was characterized by NMR, mass spectrometry and elemental analysis, and the results were as follows:

$^1$H NMR (400 MHz, CDCl$_3$) δ: 7.55 (d, J=8.9 Hz, 2H), 6.69 (d, J=8.9 Hz, 2H), 3.80 (d, J=5.7 Hz, 2H), 1.80-1.77 (m, 1H), 1.44-1.41 (m, 4H), 1.35-1.30 (m, 20H), 0.91 (t, J=6.5 Hz, 6H). $^{13}$C NMR (100 MHz, CDCl$_3$) δ: 159.47, 138.30, 117.17, 82.49, 71.22, 38.09, 32.12, 32.06, 31.56, 31.54, 30.22, 29.80, 29.55, 27.04, 27.02, 22.90, 14.33.

The results of mass spectrometry: 445.19 ([M+H]$^+$).

The results of elemental analysis: C, 59.46; H, 8.37.

Synthesis of the Compound Having the Structure of Formula (XXI-1):

In a dry Schlenk flask, p-2-hexyldecyloxy iodobenzene (3.00 g), bis(pinacolato)diboron (2.23 g) and potassium acetate (1.19 g) were dissolved in 20 mL dimethyl sulfoxide. Then the catalyst Pd(dppf)Cl$_2$ (247 mg) was added under the protection of argon gas. The reaction system was stirred at 45° C. overnight.

After completion of the reaction, the mixture was extracted three times with chloroform before the organic phase was washed with water and dried over anhydrous sodium sulfate. After solvent removal under reduced pressure, the crude product was purified by column chromatography (acetate/petroleum ether 60-90° C., 1/50, v/v) on silica gel to yield the structure of formula (XXI-1) (2.82 g, 94% yield).

The structure of the resultant compound having the structure of formula (XXI-1) was characterized by NMR, mass spectrometry and elemental analysis. The results were as follows:

$^1$H NMR (400 MHz, CDCl$_3$) δ: 7.76 (d, J=5.6 Hz, 2H), 6.90 (d, J=5.6 Hz, 2H), 3.87 (d, J=5.7 Hz, 2H), 1.81-1.78 (m, 1H), 1.50-1.39 (m, 4H), 1.34 (br, 14H), 1.28 (br, 18H), 0.90 (t, J=6.5 Hz, 6H). $^{13}$C NMR (100 MHz, CDCl$_3$) δ: 162.32, 136.69, 114.18, 83.67, 71.03, 38.20, 32.06, 31.67, 30.22, 29.89, 29.78, 29.52, 27.06, 25.07, 22.87, 14.27.

The results of mass spectrometry: 444.33 ([M$^+$]).

The results of elemental analysis: C, 75.64; H, 11.10.

Synthesis of the Compound Having the Structure of Formula (XIII-1):

In a three-necked round-bottom flask, the compound having the structure of formula (XX-1) (2.00 g), the compound having the structure of formula (XXI-1) (2.69 g) and potassium phosphate (4.78 g) were dissolved in a mixed solvent of 20 mL 1,4-dioxane and 4 mL water. Then Pd(OAc)$_2$ (20 mg) and 2-bicyclohexylphosphino-2',6'-dimethoxybiphenyl (Sphos) (37 mg), were added thereto under the protection of argon gas. The reaction system was stirred at 120° C. for 3 hours.

After completion of the reaction, the reaction system was cooled to the room temperature, and 20 mL water was added thereto. The mixed solution was extracted with chloroform three times. The organic phase was combined, and dried over anhydrous sodium sulphate. The desiccant was removed by filtration. The filtrate was concentrated, and then subjected to column chromatography by using ethyl acetate/petroleum ether (1/50 in volume) as the eluent to give 3.01 g of the compound having the structure of formula (XIII-1) with a yield of 83%.

The structure of the resultant compound having the structure of formula (XIII-1) was characterized by NMR, mass spectrometry and elemental analysis. The results were as follows:

$^1$H NMR (400 MHz, CDCl$_3$) δ: 8.69-8.66 (m, 2H), 8.15-8.12 (m, 2H), 7.91 (d, J=8.7 Hz, 1H), 7.84-8.74 (m, 3H), 7.72 (s, 1H), 7.63 (d, J=8.4 Hz, 2H), 7.10 (d, J=8.4 Hz, 2H), 4.57 (d, J=7.2 Hz, 2H), 3.96 (d, J=5.5 Hz, 2H), 2.31-2.30 (m, 1H), 1.88-1.84 (m, 1H), 1.60-1.51 (m, 4H), 1.47-1.27 (m, 30H), 1.19-1.17 (m, 14H), 0.92-0.88 (m, 6H), 0.85-0.79 (m, 6H). $^{13}$C NMR (100 MHz, CDCl$_3$) δ: 158.98, 137.48, 134.43, 132.41, 132.32, 131.48, 130.74, 130.69, 128.93, 128.24, 125.17, 125.05, 124.92, 124.65, 124.53, 123.51, 120.97, 120.74, 117.59, 116.73, 114.66, 114.21, 113.59, 71.25, 50.17, 40.07, 38.32, 32.17, 32.06, 31.99, 31.95, 31.71, 30.32, 30.13, 29.99, 29.84, 29.71, 29.61, 29.47, 27.15, 26.66, 22.95, 22.83, 14.37, 14.31, 14.26.

The results of mass spectrometry: 806.61 ([M+H]$^+$).

The results of elemental analysis: C, 86.41; H, 9.86; N, 1.73.

Synthesis of the Compound Having the Structure of Formula (XXII-1-1):

In a dry Schlenk flask, the compound having the structure of formula (XIII-1) (3.00 g) was dissolved in 20 mL tetrahydrofuran. The reaction system was cooled to 0° C. with an ice bath. Then the N-bromosuccinimide (592 mg) was added to the reaction system, and the reaction was stirred at 0° C. for 3 hours.

After completion of the reaction, 20 mL water was added to the reaction system. The mixed solution was extracted with chloroform three times. The organic phase was combined, and dried over anhydrous sodium sulphate. The desiccant was removed by filtration. The filtrate was concentrated, and then subjected to column chromatography by using ethyl acetate/petroleum ether (1/20 in volume) as the eluent to give 2.80 g of the compound having the structure of formula (XXII-1-1) with a yield of 95%.

The structure of the resultant compound having the structure of formula (XXII-1-1) was characterized by NMR, mass spectrometry and elemental analysis. The results were as follows:

$^1$H NMR (400 MHz, CDCl$_3$) δ: 8.45 (d, J=7.7 Hz, 1H), 8.36 (d, J=7.6 Hz, 1H), 8.17 (d, J=8.2 Hz, 1H), 8.13 (d, J=8.2 Hz, 1H), 7.73 (d, J=8.0 Hz, 1H), 7.69-7.66 (m, 4H), 7.51 (s, 1H), 7.20 (d, J=8.6 Hz, 2H), 4.08-4.03 (m, 4H), 2.06 (br, 1H), 1.97-1.94 (m, 1H), 1.65-1.61 (m, 4H), 1.52-1.42 (m,

20H), 1.34-1.23 (m, 24H), 1.04-1.00 (m, 6H), 0.92-0.88 (m, 6H). $^{13}$C NMR (100 MHz, CDCl$_3$) δ: 159.00, 137.61, 134.62, 132.10, 131.42, 131.18, 130.15, 129.81, 127.83, 127.47, 124.98, 124.58, 124.48, 124.26, 123.89, 121.04, 120.96, 117.09, 116.66, 116.29, 115.77, 114.64, 113.81, 71.19, 49.73, 39.77, 38.34, 32.20, 32.18, 32.07, 32.00, 31.79, 31.74, 30.35, 29.90, 29.81, 29.72, 29.64, 29.49, 27.18, 26.51, 22.98, 22.85, 14.40, 14.33, 14.28.

The results of mass spectrometry: 884.53 ([M+H]$^+$).

The results of elemental analysis: C, 78.71; H, 8.87; N, 1.59.

Synthesis of the Compound Having the Structure of (XXII-1-2):

In a three-necked round-bottom flask dried by flame, the compound having the structure of formula (XXII-1-1) (2.80 g) was dissolved in 15 mL anhydrous tetrahydrofuran. The mixture was cooled to −78° C., and 2.18 mL n-butyl lithium (1.6 mol/L in n-hexane) was added thereto under the protection of argon gas. The reaction was stirred at −78° C. for 1 h, and then the trimethyl tin chloride (693 mg) was added thereto. The mixture was stirred at room temperature overnight.

After completion of the reaction, 20 mL water was added to the reaction system. The mixed solution was extracted with chloroform three times. The organic phase was combined, and dried over anhydrous sodium sulphate. The desiccant was removed by filtration. The filtrate was concentrated to give a viscous liquid, which was directly used for the next reaction.

Synthesis of the Compound Having the Structure of Formula (XV-1):

The compound having the structure of (XXII-1-2) was dissolved in 20 mL 1,4-dioxane after sufficiently drying, and the compound 2-bromo-3-butyl ester thiophene (826 mg) and the catalyst Pd$_2$(dba)$_3$ (173 mg), P(t-Bu)$_3$ (10% by mass in hexane, 768 mg) and caesium fluoride (1.05 g) were added thereto under the protection of argon gas. The reaction system was stirred at reflux overnight.

After completion of the reaction, the reaction system was cooled to the room temperature, and 20 mL water was added thereto. The mixed solution was extracted with chloroform three times. The organic phase was combined, and dried over anhydrous sodium sulphate. The desiccant was removed by filtration. The filtrate was concentrated, and then subjected to column chromatography by using ethyl acetate/petroleum ether (1/20 in volume in volume) as the eluent to give 1.95 g of the compound having the structure of formula (XV-1) with a yield of 63%.

The structure of the resultant compound having the structure of formula (XV-1) was characterized by NMR, mass spectrometry and elemental analysis. The results were as follows:

$^1$H NMR (400 MHz, THF-d$_8$) δ: 8.76-8.70 (m, 2H), 8.14-8.11 (m, 1H), 7.95 (d, J=6.6 Hz, 1H), 7.84-7.78 (m, 2H), 7.75-7.71 (m, 2H), 7.69-7.67 (m, 1H), 7.63-7.60 (m, 2H), 7.56-7.54 (m, 1H), 7.13-7.10 (m, 2H), 4.72-4.68 (m, 2H), 4.01-3.98 (m, 2H), 3.73-3.72 (m, 2H), 2.36 (br, 1H), 1.87 (br, 1H), 1.58-1.57 (m, 3H), 1.44 (br, 12H), 1.35 (br, 18H), 1.19 (br, 20H), 0.91-0.90 (m, 6H), 0.83-0.78 (m, 8H). $^{13}$C NMR (100 MHz, THF-d$_8$) δ: 163.57, 160.10, 149.99, 139.22, 135.23, 133.93, 132.78, 132.54, 132.18, 131.73, 131.66, 130.62, 130.11, 129.23, 129.05, 125.98, 125.70, 125.57, 125.42, 124.60, 122.07, 121.72, 118.83, 117.50, 116.66, 115.36, 115.13, 79.59, 71.72, 64.53, 50.64, 40.97, 40.11, 39.87, 39.37, 35.65, 35.33, 33.07, 32.70, 32.66, 31.23, 30.91, 30.78, 30.66, 30.52, 30.40, 30.12, 29.96, 29.08, 28.05, 27.39, 24.00, 23.69, 23.33, 23.19, 21.19, 19.70, 19.65, 14.91, 14.61, 13.63, 11.90.

The results of mass spectrometry: 988.66 ([M+H]$^+$).

The results of elemental analysis: C, 81.42; H, 9.09; N, 1.44.

Synthesis of the Compound Having the Structure of Formula (XIX-1):

In a three-necked round-bottom flask dried by flame, the compound having the structure of formula (XV-1) (1.90 g) was dissolved in 30 mL tetrahydrofuran, and 4.81 mL n-octyl magnesium bromide solution (2 mol/L in tetrahydrofuran) was added thereto under the protection of argon gas. The reaction system was stirred at 90° C. overnight.

After completion of the reaction, the reaction system was cooled to 0° C., and 20 mL water was added thereto. The mixed solution was extracted with chloroform three times. The organic phase was combined, and dried over anhydrous sodium sulphate. The desiccant was removed by filtration. The filtrate was concentrated, and then subjected to column chromatography by using chloroform/petroleum ether (1/5 in volume) as the eluent to give 1.43 g of the compound having the structure of formula (XIX-1) with a yield of 65%.

The structure of the resultant compound having the structure of formula (XIX-1) was characterized by NMR, mass spectrometry and elemental analysis. The results were as follows:

$^1$H NMR (400 MHz, THF-d$_8$) δ: 8.74-8.70 (m, 2H), 8.12 (d, J=8.2 Hz, 1H), 7.99 (d, J=8.2 Hz, 1H), 7.92 (s, 1H), 7.82 (s, 1H), 7.75-7.71 (m, 2H), 7.61 (d, J=8.4 Hz, 2H), 7.47 (d, J=5.2 Hz, 1H), 7.17 (d, J=5.2 Hz, 1H), 7.11 (d, J=8.4 Hz, 2H), 4.68 (d, J=7.4 Hz, 2H), 4.00 (d, J=5.3 Hz, 2H), 2.36 (br, 1H), 2.07-2.03 (m, 2H), 1.90-1.88 (m, 2H), 1.58-1.55 (m, 2H), 1.44 (br, 12H), 1.36-1.29 (m, 24H), 1.20 (br, 18H), 1.09-0.97 (m, 12H), 0.89-0.79 (m, 20H), 0.67 (t, J=7.2 Hz, 3H). $^{13}$C NMR (100 MHz, THF-d$_8$) δ: 156.95, 149.28, 142.01, 138.67, 135.06, 133.48, 133.28, 131.72, 131.61, 130.08, 129.14, 126.17, 125.81, 125.78, 125.42, 125.28, 125.21, 124.29, 121.76, 121.50, 121.23, 118.41, 117.48, 116.23, 114.95, 114.57, 68.94, 50.72, 40.91, 32.95, 32.89, 32.82, 32.77, 31.04, 30.80, 30.75, 30.58, 30.50, 30.36, 27.47, 26.93, 23.71, 23.63, 14.60, 14.58.

The results of mass spectrometry: 1142.85 ([M+H]$^+$).

The results of elemental analysis: C, 83.04; H, 10.13; N, 1.24.

Synthesis of the Compound Having the Structure of Formula (XVI-1):

In a dry three-necked round-bottom flask, the compound having the structure of formula (XIX-1) (1.43 g) was dissolved in 30 mL toluene. Then the solid acid catalyst Amberlyst 15 (600 mg) was added thereto. The mixture was stirred at reflux under the protection of argon gas overnight.

After completion of the reaction, the reaction system was cooled to the room temperature, and 20 mL water was added thereto. The mixed solution was extracted with chloroform three times. The organic phase was combined, and dried over anhydrous sodium sulphate. The desiccant was removed by filtration. The filtrate was concentrated, and then subjected to column chromatography by using petroleum ether (boiling temperature: 60-90° C.) as the eluent to give 843 mg of the compound having the structure of formula (XVI-1) with a yield of 63%.

The structure of the resultant compound having the structure of formula (XVI-1) was characterized by NMR, mass spectrometry and elemental analysis. The results were as follows:

¹H NMR (400 MHz, THF-d₈) δ: 8.74 (dd, $J_1$=10.1 Hz, $J_2$=2.6 Hz, 2H), 8.43 (d, J=7.9 Hz, 1H), 8.13 (d, J=8.1 Hz, 1H), 7.93-7.89 (m, 1H), 7.87 (s, 1H), 7.77-7.73 (m, 1H), 7.62 (d, J=7.9 Hz, 2H), 7.51 (d, J=4.8 Hz, 1H), 7.19 (d, J=4.0, 1H), 7.12 (d, J=7.9 Hz, 2H), 5.06 (d, J=7.4 Hz, 2H), 3.99 (d, J=5.0 Hz, 2H), 2.58-2.54 (m, 3H), 2.47-2.40 (m, 2H), 1.87 (br, 1H), 1.57-1.55 (m, 6H), 1.45-1.28 (m, 28H), 1.15-1.05 (m, 34H), 0.93-0.89 (m, 6H), 0.82-0.74 (m, 16H). ¹³C NMR (100 MHz, THF-d₈) δ: 160.05, 155.24, 142.45, 140.21, 138.13, 135.27, 134.62, 133.94, 132.40, 132.15, 131.99, 131.41, 129.25, 127.60, 125.85, 125.78, 125.73, 125.56, 125.40, 125.13, 123.08, 121.71, 121.40, 118.92, 118.27, 116.15, 115.39, 71.65, 54.10, 40.63, 40.37, 39.33, 33.06, 32.89, 32.63, 31.23, 31.04, 30.90, 30.78, 30.56, 30.50, 30.40, 28.03, 27.96, 25.16, 23.77, 23.63, 23.58, 14.69, 14.62, 14.56.

The results of mass spectrometry: 1124.85 ([M+H]⁺).

The results of elemental analysis: C, 84.34; H, 10.13; N, 1.24.

Synthesis of the Compound Having the Structure of Formula (XXIII-1):

In a three-necked round-bottom flask dried by flame, the compound having the structure of formula (XVI-1) (800 mg) was dissolved in 15 mL anhydrous tetrahydrofuran. The mixture was cooled to –78° C., and t-butyl lithium (0.66 mL, 1.3 mol/L in n-hexane) was added thereto under the protection of argon gas. The reaction was stirred at –78° C. for 1 h, and then trimethyl tin chloride (169 mg) was added thereto. The mixture was stirred at room temperature overnight.

After completion of the reaction, 20 mL water was added to the reaction system. The mixed solution was extracted with chloroform three times. The organic phase was combined, and dried over anhydrous sodium sulphate. The desiccant was removed by filtration. The filtrate was concentrated to give a viscous liquid, which was directly used for the next reaction.

Synthesis of the Compound Having the Structure of Formula (X-1):

The compound having the structure of formula (XXIII-1) was dissolved in 20 mL 1,4-dioxane after sufficiently drying. Then the compound having the structure of formula (XVIII-1) (500 mg) and the catalyst Pd(PPh₃)₂Cl₂ (60 mg) were added thereto under the protection of argon gas. The reaction system was stirred at reflux overnight.

After completion of the reaction, the reaction system was cooled to the room temperature, and 20 mL water was added thereto. The mixed solution was extracted with chloroform three times. The organic phases were combined, and dried over anhydrous sodium sulphate. The desiccant was removed by filtration. The filtrate was concentrated, and then subjected to column chromatography by using ethyl acetate/petroleum ether (1/20 in volume) as the eluent to give 825 mg of the compound having the structure of formula (X-1) with a yield of 81%.

The structure of the resultant compound having the structure of formula (X-1) was characterized by NMR, mass spectrometry and elemental analysis. The characterization data of NMR were as follows:

¹H NMR (400 MHz, THF-d₈) δ: 8.75 (m, 2H), 8.54 (m, 1H), 8.51 (s, 1H), 8.18 (m, 6H), 7.98 (m, 3H), 7.77 (m, 1H), 7.62 (d, J=7.8 Hz, 2H), 7.13 (d, J=8.6 Hz, 2H), 5.09 (m, 2H), 4.36 (t, J=6.5 Hz, 2H), 4.00 (d, J=5.0 Hz, 2H), 2.66 (m, 2H), 2.58 (m, 3H), 1.88 (m, 1H), 1.79 (m, 2H), 1.54 (m, 6H), 1.46-1.29 (m, 30H), 1.17 (m, 20H), 1.04 (m, 20H), 0.91 (m, 8H), 0.80-0.74 (m, 7H), 0.69 (t, J=6.4 Hz, 6H). ¹³C NMR (100 MHz, CDCl₃) δ: 166.54, 160.11, 156.18, 154.91, 153.63, 145.42, 142.55, 142.17, 140.88, 138.69, 135.16, 134.44, 132.27, 132.17, 131.99, 131.26, 130.94, 130.39, 129.93, 129.72, 129.25, 126.12, 125.81, 125.67, 125.59, 125.28, 124.81, 123.28, 122.56, 121.95, 121.52, 119.01, 118.87, 116.16, 115.42, 71.68, 65.40, 67.15, 54.18, 40.69, 40.45, 39.34, 33.06, 32.94, 32.89, 32.63, 32.04, 31.24, 30.90, 30.82, 30.78, 30.60, 30.50, 30.45, 30.39, 28.03, 25.40, 23.76, 23.64, 23.55, 20.37, 14.67, 14.62, 14.56, 14.50, 14.36.

The results of mass spectrometry: 1435.95 ([M+H]⁺).

The results of elemental analysis: C, 80.34; H, 8.91; N, 2.91.

Synthesis of the Compound Having the Structure of Formula (X):

In a three-necked round-bottom flask, the compound having the structure of formula (X-1) (600 mg) was dissolved in 15 mL tetrahydrofuran and 5 mL water. Then the potassium hydroxide (235 mg) was added to the reaction system. The mixture was stirred at 80° C. for 5 hours.

After completion of the reaction, the reaction system was cooled to the room temperature, and 20 mL aqueous phosphoric acid solution (0.2 mol/L) was added thereto. The mixed solution was extracted with chloroform three times. The organic phase was combined, and dried over anhydrous sodium sulphate. The desiccant was removed by filtration. The filtrate was concentrated, and then subjected to column chromatography by using trichloromethane/methanol (1/20 in volume) as the eluent to give 549 mg of the compound having the structure of formula (X) with a yield of 95%.

The structure of the resultant compound having the structure of formula (X) was characterized by NMR, mass spectrometry and elemental analysis. The results were as follows:

¹H NMR (400 MHz, THF-d₈) δ: 8.82-8.77 (m, 2H), 8.55 (d, J=8.0 Hz, 1H), 8.50 (s, 1H), 8.22-8.16 (m, 5H), 8.13 (d, J=8.2 Hz, 1H), 8.01-7.97 (m, 2H), 7.80 (s, 1H), 7.78 (t, J=7.8 Hz, 1H), 7.61 (d, J=8.28 Hz, 2H), 7.13 (d, J=8.4 Hz, 2H), 5.09 (d, J=7.6 Hz, 2H), 4.01 (d, J=5.2 Hz, 2H), 2.70-2.53 (m, 4H), 2.09-2.02 (m, 1H), 1.89 (br, 1H), 1.58-1.52 (m, 4H), 1.46-1.29 (m, 32H), 1.16-1.12 (m, 18H), 1.04 (br, 14H), 0.93-0.89 (m, 10H), 0.82-0.74 (m, 6H), 0.69 (t, J=6.1 Hz, 6H). ¹³C NMR (100 MHz, THF-d₈) δ: 167.75, 160.09, 156.17, 154.91, 153.62, 145.34, 142.30, 142.23, 140.84, 138.67, 135.16, 134.47, 134.40, 132.27, 132.18, 131.97, 131.33, 131.25, 131.07, 130.70, 129.84, 129.65, 129.25, 129.13, 126.12, 125.80, 125.66, 125.58, 125.28, 124.82, 123.30, 122.51, 121.94, 121.49, 119.15, 118.87, 116.14, 115.41, 71.64, 57.15, 54.18, 40.68, 40.47, 39.33, 33.05, 32.90, 32.63, 31.24, 31.13, 30.90, 30.81, 30.61, 30.46, 30.40, 28.02, 25.42, 23.77, 23.65, 23.55, 14.69, 14.64, 14.58, 14.51.

The results of high resolution mass spectrometry: 1377.86678.

The results of elemental analysis: C, 80.14; H, 8.69; N, 3.10.

The above experimental results indicated that the compound represented by formula (X) was prepared in the present invention.

Example 2

Scheme 2
Preparation of the compound having the structure of formula (XI)

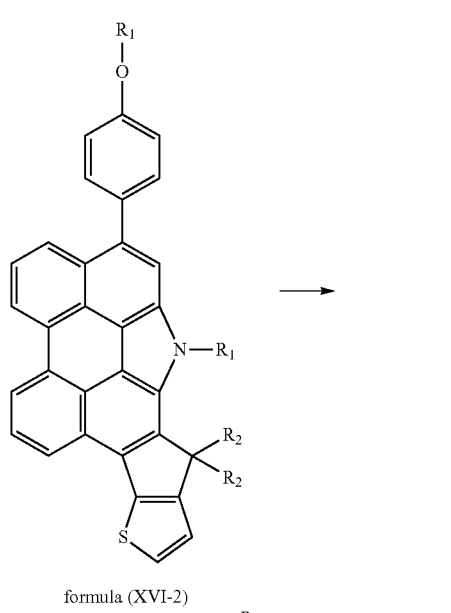

formula (XVI-2)

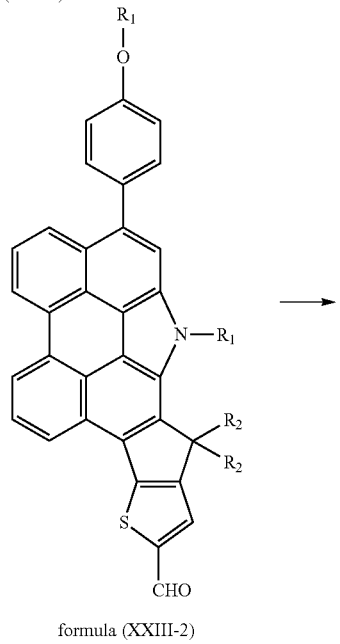

formula (XXIII-2)

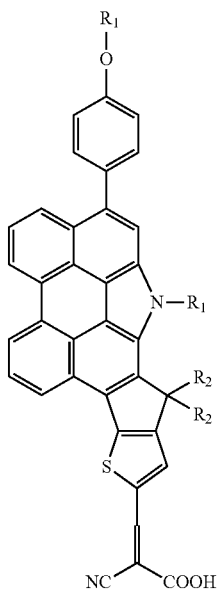

formula (XI)

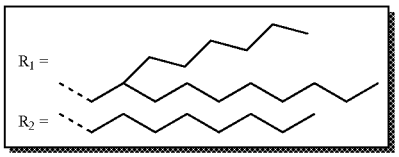

Preparation of the Compound Having the Structure of Formula (XXIII-2):

In a dry Schlenk flask, of the compound having the structure of formula (XVI-2) (340 mg) was dissolved in 20 mL 1, 2-dichloroethane. The reaction system was cooled to 0° C. with an ice bath. 0.15 mL of N, N-dimethyl formamide and 0.046 mL phosphorus oxychloride were added to the reaction system. The mixture was stirred at 40° C. overnight.

After completion of the reaction, the reaction system was cooled to the room temperature, and 20 mL water was added thereto. The mixture was stirred for 2 hours, and then extracted with chloroform three times. The organic phase was combined, and dried over anhydrous sodium sulphate. The desiccant was removed by filtration. The filtrate was concentrated, and then subjected to column chromatography by using ethyl acetate/petroleum ether (1/20 in volume) as the eluent to give 294 mg of the compound having the structure of formula (XXIII-2) with a yield of 85%.

The structure of the compound having the structure of formula (XXIII-2) was characterized by NMR, mass spectrometry and elemental analysis. The results were as follows:

$^1$H NMR (400 MHz, THF-d$_8$) δ: 9.97 (s, 1H), 8.81 (d, J=7.7 Hz, 1H), 8.79 (d, J=7.6 Hz, 1H), 8.48 (d, J=8.1 Hz, 1H), 8.16 (d, J=8.2 Hz, 1H), 7.99 (t, J=7.9 Hz, 1H), 7.05 (s, 1H), 7.91 (s, 1H), 7.79 (t, J=7.8 Hz, 1H), 7.62 (d, J=8.4 Hz, 2H), 7.14 (d, J=8.4 Hz, 2H), 5.08 (d, J=7.7 Hz, 2H), 3.99 (d,

J=5.2 Hz, 2H), 2.60-2.59 (m, 3H), 1.87-1.86 (m, 1H), 1.57-1.55 (m, 4H), 1.51-1.45 (m, 6H), 1.35-1.25 (m, 24H), 1.15-1.04 (m, 36H), 0.92-0.86 (m, 10H), 0.82-0.75 (m, 12H). $^{13}$C NMR (100 MHz, THF-d$_8$) δ: 182.59, 160.21, 155.22, 152.05, 146.34, 143.45, 139.68, 135.08, 134.92, 132.70, 132.14, 131.72, 131.09, 129.91, 129.24, 126.72, 125.88, 125.79, 125.60, 122.92, 122.37, 121.89, 120.19, 118.59, 116.18, 115.45, 71.67, 56.96, 54.19, 40.67, 40.15, 39.32, 33.06, 33.04, 33.00, 32.92, 32.86, 32.62, 31.22, 31.01, 30.89, 30.77, 30.55, 30.50, 30.35, 28.02, 27.94, 23.77, 23.75, 23.62, 23.56, 14.68, 14.61, 14.54.

The results of mass spectrometry: 1152.85 ([M+H]$^+$).

The results of elemental analysis: C, 83.35; H, 9.88; N, 1.21.

Synthesis of the Compound Having the Structure of Formula (XI):

In a dry two-necked round-bottom flask, the compound having the structure of formula (XXIII-2) (250 mg) was dissolved in a mixed solvent of acetonitrile and dichloromethane (1/2 in volume). Then cyanoacrylic (94 mg) acid and ammonium acetate (55 mg) were added thereto. The reaction system was stirred at refluxor 48 hours.

After completion of the reaction, the temperature of the reaction system was cooled to the room temperature. After the addition of 30 mL distilled water, the mixture was extracted with chloroform three times. The organic phases were combined, and dried over anhydrous sodium sulphate. The desiccant was removed by filtration. The filtrate was concentrated, and then subjected to column chromatography by using methanol/chloroform (1/20 in volume) as the eluent to give the compound having the structure of formula (XI). Thereafter, the compound having the structure of the structure of formula (XI) was dissolved in chloroform. The mixture was washed with 0.2 mol/L of aqueous phosphoric acid solution and distilled water sequentially for several times. The organic phase was concentrated, and dried under reduced pressure to give 251 mg of the compound having the structure of formula (XI) as a purple solid with a yield of 98%.

The structure of the resultant compound having the structure of formula (XI) was characterized by NMR, mass spectrometry and elemental analysis. The results were as follows:

$^1$H NMR (400 MHz, THF-d$_8$) δ: 8.87 (d, J=7.7 Hz, 1H), 8.83 (d, J=7.6 Hz, 1H), 8.49-8.47 (m, 2H), 8.15 (d, J=8.2 Hz, 1H), 8.06 (t, J=7.8 Hz, 1H), 7.98 (s, 1H), 7.89 (s, 1H), 7.81 (t, J=7.9 Hz, 1H), 7.61 (d, J=8.6 Hz, 2H), 7.13 (d, J=8.6 Hz, 2H), 5.06 (d, J=7.9 Hz, 2H), 4.01 (d, J=5.5 Hz, 2H), 2.57-2.52 (m, 4H), 2.09-2.01 (m, 1H), 1.89-1.86 (m, 1H), 1.61-1.56 (m, 4H), 1.45-1.29 (m, 32H), 1.14-1.04 (m, 32H), 0.92-0.85 (m, 10H), 0.81-0.79 (m, 3H), 0.78-0.72 (m, 9H). $^{13}$C NMR (100 MHz, THF-d$_8$) δ: 165.79, 160.23, 155.55, 152.84, 146.07, 143.33, 139.77, 139.49, 135.24, 134.93, 133.04, 132.13, 131.77, 131.11, 130.70, 130.68, 130.36, 129.25, 126.96, 125.91, 125.79, 125.59, 125.47, 123.12, 122.40, 122.04, 120.40, 118.62, 118.37, 116.17, 115.45, 71.70, 56.91, 54.17, 46.11, 40.68, 40.18, 39.33, 36.38, 33.07, 33.05, 32.97, 32.92, 32.87, 32.63, 31.23, 31.02, 30.99, 30.89, 30.80, 30.71, 30.64, 30.55, 30.50, 30.42, 30.36, 28.18, 28.03, 28.02, 27.92, 23.77, 23.75, 23.62, 23.57, 14.65, 14.63, 14.59, 14.53.

The results of high resolution mass spectrometry: 1218.85502.

The results of elemental analysis: C, 81.72; H, 9.42; N, 2.30.

The above experimental results indicated that the compound represented by formula (XI) was prepared in the present invention.

Example 3

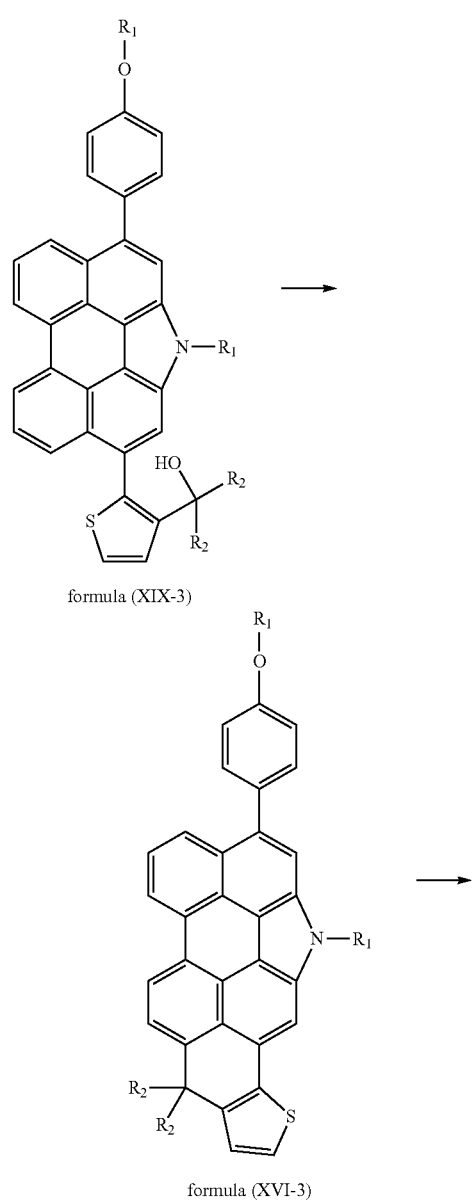

Scheme 3 formula (XIX-3)

formula (XVI-3)

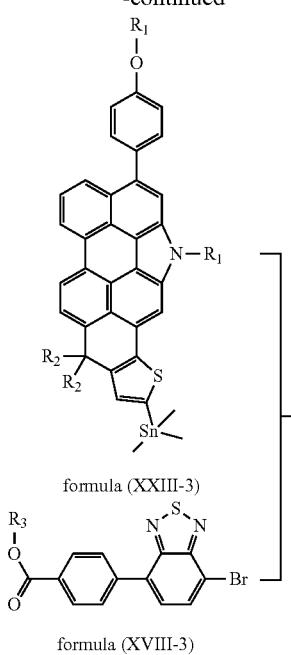

formula (XXIII-3)

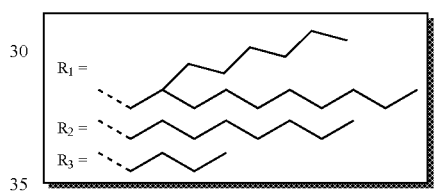

formula (XVIII-3)

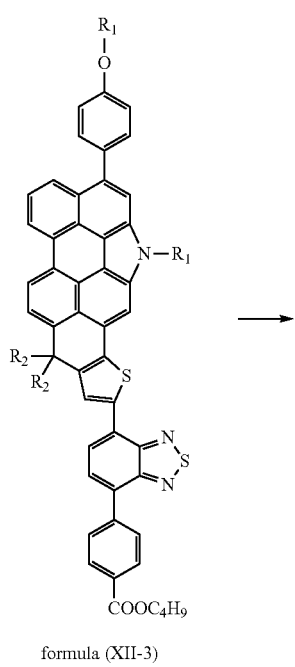

formula (XII-3)

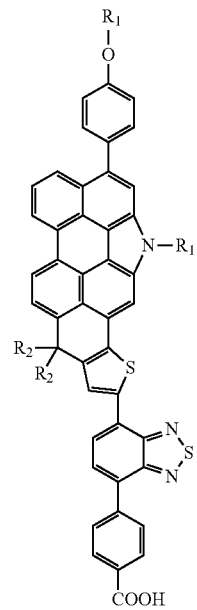

formula (XII)

Synthesis of the Compound Having the Structure of Formula (XVI-3):

In a dry three-necked round-bottom flask, the compound having the structure of formula (XIX-3) (1.43 g) was dissolved in 30 mL toluene. Then the solid acid catalyst Amberlyst 15 (600 mg) was added thereto. The mixture was stirred at reflux under the protection of argon gas overnight.

After completion of the reaction, the reaction system was cooled to the room temperature, and 20 mL water was added thereto. The mixed solution was extracted with chloroform three times. The organic phases were combined, and dried over anhydrous sodium sulphate. The desiccant was removed by filtration. The filtrate was concentrated, and then subjected to column chromatography by using petroleum ether (boiling temperature: 60-90° C.) as the eluent to give 421 mg of the compound having the structure of formula (XVI-3) with a yield of 31%.

The structure of the resultant compound having the structure of formula (XVI-3) was characterized by NMR, mass spectrometry and elemental analysis. The characterization data of NMR were as follows:

$^1$H NMR (400 MHz, THF-$d_8$) δ: 8.71-8.67 (m, 1H), 8.63-8.60 (m, 1H), 8.08 (d, J=8.2 Hz, 1H), 7.90 (s, 1H), 7.75-7.74 (m, 2H), 7.70-7.68 (m, 1H), 7.60 (d, J=8.1 Hz, 2H), 7.34-7.33 (m, 1H), 7.19-7.17 (m, 1H), 7.09 (d, J=6.6 Hz, 2H), 4.62-4.58 (m, 2H), 3.96 (br, 2H), 2.36 (br, 1H), 2.36-2.05 (m, 4H), 1.84 (br, 1H), 1.56 (br, 2H), 1.44 (br, 12H), 1.35-1.28 (m, 20H), 1.22-1.13 (m, 18H), 1.05-0.99 (m, 14H), 0.93-0.89 (m, 8H), 0.85-0.75 (m, 16H). $^{13}$C NMR (100 MHz, THF-$d_8$) δ: 159.95, 144.35, 141.17, 139.28, 138.02, 135.40, 133.61, 132.16, 131.82, 129.39, 128.96, 127.75, 126.22, 126.00, 125.41, 125.03, 124.75, 123.80, 123.34, 122.31, 121.18, 118.27, 118.12, 115.33, 115.03, 106.23, 71.66, 50.50, 49.37, 48.25, 40.91, 39.34, 33.06, 33.00, 32.96, 32.88, 32.73, 32.63, 31.24, 31.11, 30.90, 30.78, 30.71, 30.51, 30.42, 30.33, 28.03, 27.51, 27.44, 25.97, 23.77, 23.69, 23.58, 14.69, 14.60.

The results of mass spectrometry: 1124.85 ([M+H]$^+$).

The results of elemental analysis: C, 84.34; H, 10.13; N, 1.24.

Synthesis of the Compound Having the Structure of Formula (XXIII-3):

In a three-necked round-bottom flask dried by flame, the compound having the structure of formula (XVI-3) (400 mg) was dissolved in 15 mL anhydrous tetrahydrofuran. The mixture was cooled to −78° C., and then 0.33 mL t-butyl lithium (1.3 mol/L in n-hexane) was added thereto under the protection of argon gas. The reaction was stirred at −78° C. for 1 h, and then trimethyl tin chloride (85 mg) was added thereto. The mixture was stirred at room temperature overnight.

After completion of the reaction, 20 mL water was added to the reaction system. The mixed solution was extracted with chloroform three times. The organic phase was combined, and dried over anhydrous sodium sulphate. The desiccant was removed by filtration. The filtrate was concentrated to give a viscous liquid, which was directly used for the next reaction.

Synthesis of the Compound Having the Structure of Formula (XII-3):

The compound having the structure of formula (XXIII-3) was dissolved in 20 mL 1,4-dioxane after sufficiently drying. Then the compound having the structure of formula (XVIII-3) (250 mg) and catalyst Pd$_2$(PPh)$_2$Cl$_2$ (30 mg) were added thereto under the protection of argon gas. The reaction system was stirred at reflux overnight.

After completion of the reaction, the reaction system was cooled to the room temperature, and 20 mL water was added thereto. The mixed solution was extracted with chloroform three times. The organic phase was combined, and dried over anhydrous sodium sulphate. The desiccant was removed by filtration. The filtrate was concentrated, and then subjected to column chromatography by using ethyl acetate/petroleum ether (1/20 in volume) as the eluent to give 412 mg of the compound having the structure of formula (XII-3) with a yield of 81%.

The structure of the resultant compound having the structure of formula (XII-3) was characterized by NMR, mass spectrometry and elemental analysis. The characterization data of NMR were as follows:

$^1$H NMR (400 MHz, THF-d$_8$) δ: 8.79 (d, J=8.1 Hz, 1H), 8.68 (d, J=7.4 Hz, 1H), 8.54 (m, 1H), 8.16-8.08 (m, 5H), 8.01 (d, J=6.4 Hz, 1H), 7.95 (s, 1H), 7.90 (d, J=8.1 Hz, 1H), 7.80 (d, J=6.2 Hz, 1H), 7.74 (m, 1H), 7.62 (s, 1H), 7.55 (d, J=8.4 Hz, 2H), 7.08 (d, J=8.6 Hz, 2H), 4.44 (m, 2H), 4.36 (t, J=6.4 Hz, 2H), 3.98 (d, J=5.3 Hz, 2H), 2.50-2.40 (m, 2H), 2.31 (m, 3H), 1.87 (m, 1H), 1.78 (m, 2H), 1.57-1.28 (m, 37H), 1.22 (m, 20H), 1.06 (m, 18H), 0.92 (m, 8H), 0.79 (t, J=6.3 Hz, 6H), 0.70 (t, J=4.8 Hz, 6H). $^{13}$C NMR (100 MHz, CDCl$_3$) δ: 166.51, 159.99, 154.84, 153.75, 145.60, 142.47, 141.82, 140.91, 138.44, 137.53, 135.26, 133.83, 133.68, 132.17, 131.72, 131.62, 131.12, 130.68, 130.42, 130.04, 129.71, 129.57, 129.40, 129.22, 129.08, 128.25, 127.11, 126.30, 125.94, 125.63, 125.49, 124.98, 124.93, 123.41, 122.58, 121.36, 118.59, 118.15, 115.31, 114.97, 106.95, 71.69, 65.43, 50.59, 49.35, 48.42, 40.74, 39.36, 33.08, 33.06, 33.01, 32.96, 32.89, 32.69, 32.63, 32.03, 31.24, 31.13, 30.91, 30.79, 30.70, 30.51, 30.45, 30.38, 30.36, 28.05, 28.03, 27.43, 27.39, 26.17, 23.78, 23.76, 23.70, 23.66, 23.55, 20.37, 14.47, 14.66, 14.62, 14.50, 14.35.

The results of mass spectrometry: 1435.95 ([M+H]$^+$).

The results of elemental analysis: C, 80.34; H, 8.91; N, 2.91.

Synthesis of the Compound Having the Structure of the Structure of Formula (XII):

In a three-necked round-bottom flask, the compound having the structure of formula (XII-3) (300 mg) was dissolved in 15 mL tetrahydrofuran and 5 mL water. Then the potassium hydroxide (117 mg) was added to the reaction system. The mixture was stirred at 80° C. for 5 hours.

After completion of the reaction, the reaction system was cooled to the room temperature, and 20 mL of aqueous phosphoric acid solution (0.2 mol/L) was added thereto. The mixed solution was extracted with chloroform three times. The organic phase was combined, and dried over anhydrous sodium sulphate. The desiccant was removed by filtration. The filtrate was concentrated, and then subjected to column chromatography by using trichloromethane/methanol (1/20 in volume) as the eluent to give 274 mg of the compound having the structure of formula (XII) with a yield of 95%.

The structure of the compound having the structure of formula (XII) was characterized by NMR, mass spectrometry and elemental analysis. The results were as follows:

$^1$H NMR (400 MHz, THF-d$_8$) δ: 8.80 (d, J=8.0 Hz, 1H), 8.69 (d, J=7.5 Hz, 1H), 8.53 (s, 1H), 8.21-8.16 (m, 5H), 8.09 (d, J=8.2 Hz, 1H), 8.06 (s, 1H), 7.97 (d, J=7.5 Hz, 1H), 7.90 (d, J=8.0 Hz, 1H), 7.77-7.72 (m, 2H), 7.60 (d, J=8.3 Hz, 2H), 7.10 (d, J=8.4 Hz, 2H), 4.69 (d, J=6.7 Hz, 2H), 4.00 (d, J=5.3 Hz, 2H), 2.43-2.29 (m, 6H), 2.08-2.02 (m, 1H), 1.88-1.84 (m, 1H), 1.57-1.46 (m, 14H), 1.36-1.26 (m, 30H), 1.19-1.14 (m, 8H), 1.05 (br, 18H), 0.93-0.89 (m, 6H), 0.80-0.77 (m, 6H), 0.70 (t, J=6.5 Hz, 6H). $^{13}$C NMR (100 MHz, THF-d$_8$) δ: 167.73, 159.96, 154.82, 153.73, 145.59, 142.19, 141.74, 140.93, 138.39, 137.59, 135.24, 133.78, 133.67, 132.16, 131.72, 131.57, 130.73, 129.96, 129.49, 129.38, 129.16, 129.06, 128.11, 127.13, 126.29, 125.92, 125.63, 125.49, 124.92, 123.41, 122.57, 121.36, 118.55, 118.13, 115.31, 114.94, 106.93, 71.67, 50.56, 49.34, 48.42, 40.70, 39.34, 33.05, 32.99, 32.94, 32.88, 32.62, 31.23, 32.12, 30.90, 30.77, 30.69, 30.50, 30.40, 30.36, 28.03, 27.40, 26.19, 23.76, 23.69, 23.54, 14.67, 14.51.

The results of high resolution mass spectrometry: 1377.86678.

The results of elemental analysis: C, 80.14; H, 8.69; N, 3.10.

The above experimental results indicated that the compound represented by formula (XII) was prepared in the present invention.

Example 4

An organic dye-sensitized solar cell was assembled in accordance with the document (*Energy Environ. Sci.*, 2010, 3, 1924), specifically as follows.

The organic dyes produced in Examples 1 to 3 (i.e. the compound having the structure of formula (X), the compound having the structure of formula (XI) and the compound having the structure of formula (XII)) were prepared into a 150 μmol/L ethanol/toluene (9/1 in volume) solution, respectively.

A bilayer membrane electrode with a TiO$_2$ structure was immersed in the solution for 12 hours. Then, the electrode was taken out. A glass electrode coated with nanoplatinium was sealed annularly by a hot melt method. At last, an electrolyte was filled into the gap between the two electrodes, thereby dye-sensitized solar cells were constructed.

Under the simulated AM1.5G sunlight at 100 mW cm$^{-2}$, the produced dye-sensitized solar cells were detected for the performance. The test results are in Table 1. Table 1 shows the results of the performance tests of the dye-sensitized solar cells made from the organic dyes according to the Examples of the invention.

TABLE 1 the results of the performance tests of the dye-sensitized solar cells made from the organic dyes according to the examples of the invention

| Organic dyes | Short circuit current [mA cm$^{-2}$] | Open circuit voltage [mV] | Filling factor | Cell Efficiency [%] |
|---|---|---|---|---|
| X | 17.95 | 850 | 0.740 | 11.5 |
| XI | 13.69 | 832 | 0.758 | 8.63 |
| XII | 17.64 | 823 | 0.724 | 10.5 |

The description of the above Examples is only for the purpose of helping the reader to understand the process of the present invention and the key idea thereof. It should be understood that many changes and modifications may be made by those skilled in the art without deviating from the principle of the present invention. Those changes and modifications also fall into the protection scope of the claims of the present invention.

The invention claimed is:

1. An organic dye having the structure of formula (I) or formula (II):

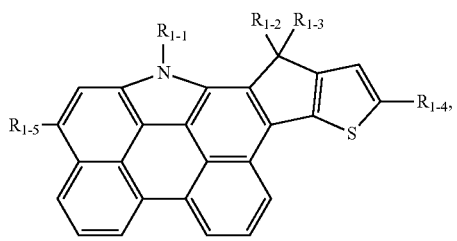

(I)

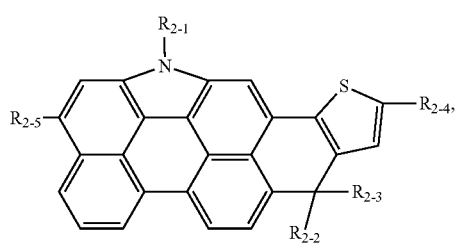

(II)

wherein $R_{1-1}$ and $R_{2-1}$ are independently selected from $C_1$-$C_{36}$ alkyl;

$R_{1-2}$, $R_{1-3}$, $R_{2-2}$, and $R_{2-3}$ are independently selected from H, $C_1$-$C_{36}$ alkyl, phenyl substituted with $C_1$-$C_{36}$ alkyl, and phenyl substituted with $C_1$-$C_{36}$ alkoxy;

$R_{1-4}$ and $R_{2-4}$ are independently selected from formula (III), formula (IV), formula (V), and formula (VI):

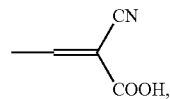

(III)

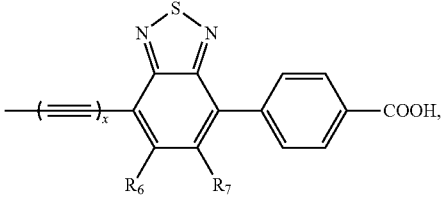

(IV)

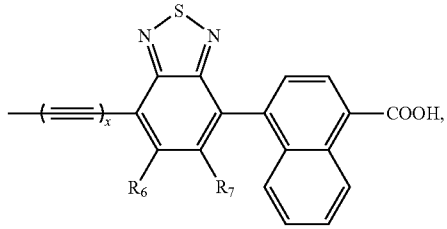

(V)

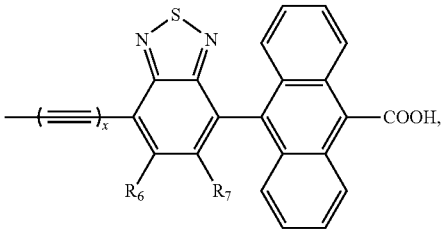

(VI)

wherein $R_6$ and $R_7$ are independently selected from H, F, $C_1$-$C_{36}$ alkyl, phenyl substituted with $C_1$-$C_{36}$ alkyl, and phenyl substituted with $C_1$-$C_{36}$ alkoxy; and x is 0 or 1; and $R_{1-5}$ and $R_{2-5}$ are independently selected from H, aryl, and $C_1$-$C_{36}$ alkyl.

2. The organic dye according to claim 1, wherein the aryl is aryl substituted with $C_1$-$C_{36}$ alkyl or aryl substituted with $C_1$-$C_{36}$ alkoxy.

3. The organic dye according to claim 1, wherein the aryl is selected from formula (VII), formula (VIII), and formula (IX):

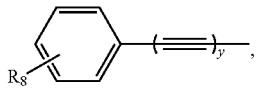

(VII)

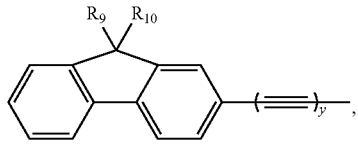

(VIII)

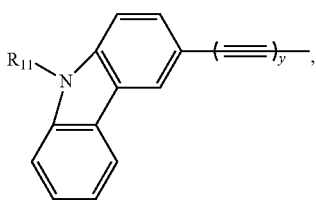

(IX)

wherein
R₈ is H, $C_1$-$C_{36}$ alkyl, or $C_1$-$C_{36}$ alkoxy;
R₉, R₁₀, and R₁₁ are independently selected from H and $C_1$-$C_{36}$ alkyl; and
y is 0 or 1.

4. The organic dye according to claim 1, wherein said $R_{1-1}$ and $R_{2-1}$ are independently selected from $C_3$-$C_{30}$ alkyl.

5. The organic dye according to claim 1, wherein said $R_{1-2}$, $R_{1-3}$, $R_{2-2}$, and $R_{2-3}$ are independently selected from H, $C_3$-$C_{30}$ alkyl, phenyl substituted with $C_3$-$C_{30}$ alkyl, and phenyl substituted with $C_3$-$C_{30}$ alkoxy.

6. The organic dye according to claim 1, wherein said organic dye has the structure of formula (X), formula (XI) or formula (XII):

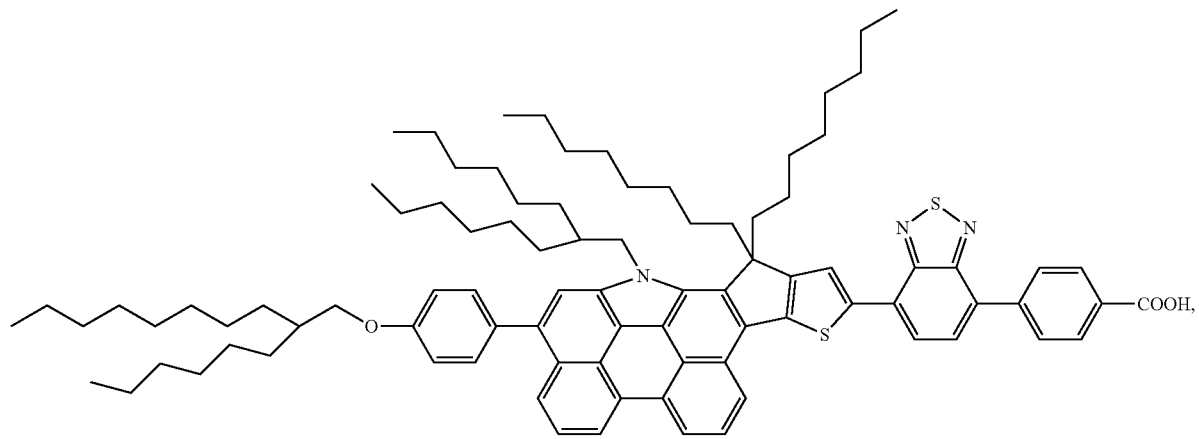
(X)

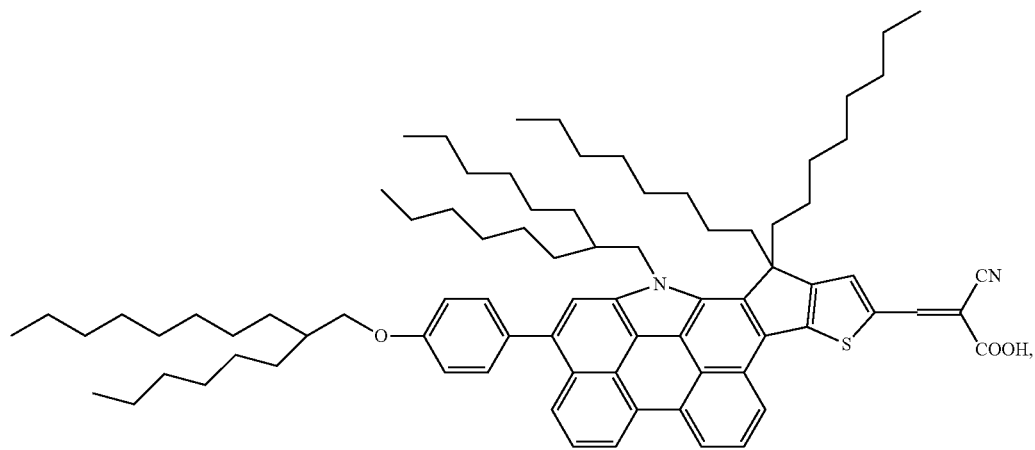
(XI)

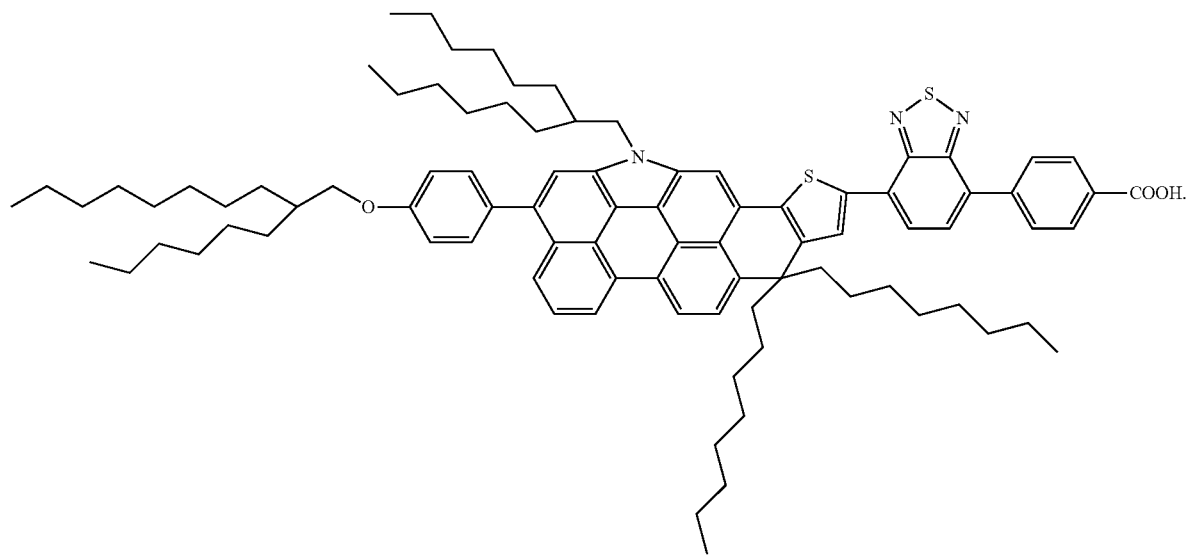
(XII)

7. A process for producing an organic dye comprising:

1) reacting a compound having the structure of formula (XIII) with a compound having the structure of formula (XIV) to give a compound having the structure of formula (XV),

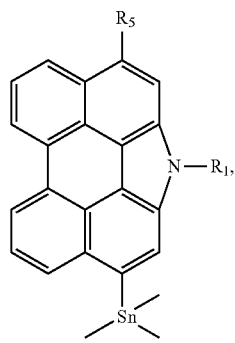

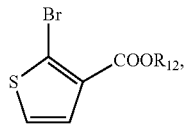

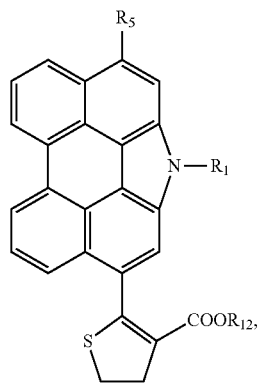

wherein
 $R_1$ is $C_1$-$C_{36}$ alkyl;
 $R_5$ is H, aryl or $C_1$-$C_{36}$ alkyl; and
 $R_{12}$ is $C_1$-$C_8$ alkyl; and 2) converting the compound having the structure of formula (XV) into a compound having the structure of formula (I) or formula (II):

(I)
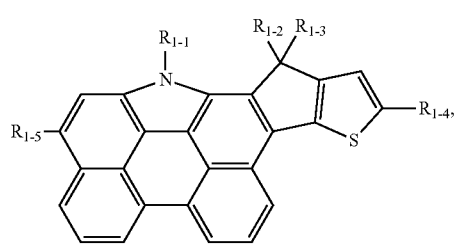

(II)
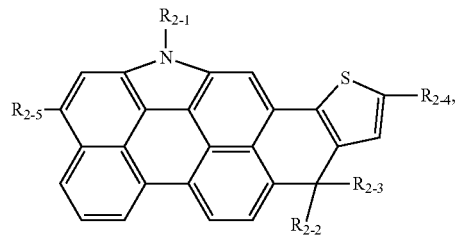

wherein
 $R_{1-1}$ and $R_{2-1}$ are independently selected from $C_1$-$C_{36}$ alkyl;
 $R_{1-2}$, $R_{1-3}$, $R_{2-2}$, and $R_{2-3}$ are independently selected from H, $C_1$-$C_{36}$ alkyl, phenyl substituted with $C_1$-$C_{36}$ alkyl and phenyl substituted with $C_1$-$C_{36}$ alkoxy;
 $R_{1-4}$ and $R_{2-4}$ are independently selected from formula (III), formula (IV), formula (V), and formula (VI):

(III)

(IV)
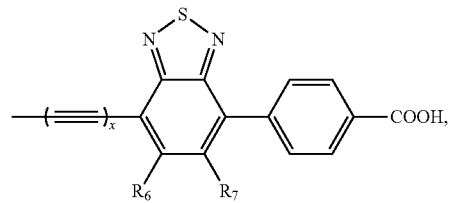

(V)
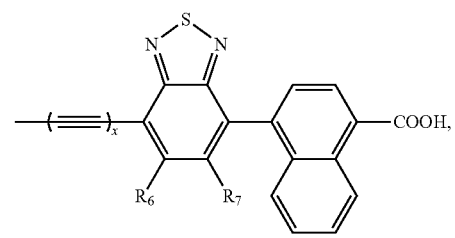

(VI)
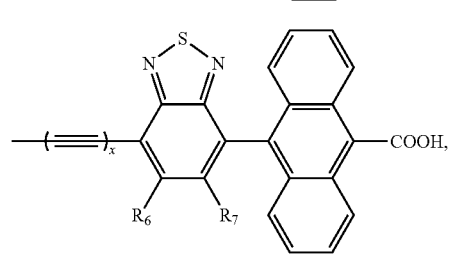

wherein $R_6$ and $R_7$ are independently selected from H, F, $C_1$-$C_{36}$ alkyl, phenyl substituted with $C_1$-$C_{36}$ alkyl, and phenyl substituted with $C_1$-$C_{36}$ alkoxy; and x is 0 or 1; and
 $R_{1-5}$ and $R_{2-5}$ are independently selected from hydrogen, aryl, and $C_1$-$C_{36}$ alkyl.

8. The process according to claim 7, wherein said step 2) is performed as follows:

2-1) converting the compound having the structure of formula (XV) into a compound having the structure of formula (XVI) or formula (XVII):

(XVI)

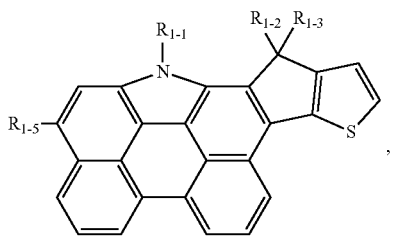

(XVII)

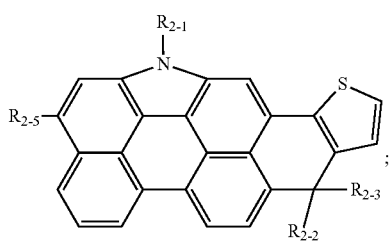

wherein
R$_{1-1}$ and R$_{2-1}$ are independently selected from C$_1$-C$_{36}$ alkyl;
R$_{1-2}$, R$_{1-3}$, R$_{2-2}$, and R$_{2-3}$ are independently selected from H, C$_1$-C$_{36}$ alkyl, phenyl substituted with C$_1$-C$_{36}$ alkyl and phenyl substituted with C$_1$-C$_{36}$ alkoxy;
R$_{1-5}$ and R$_{2-5}$ are selected from H, aryl, and C$_1$-C$_{36}$ alkyl; and 2-2) reacting the compound having the structure of formula (XVI) or formula (XVII) with a compound having the structure of formula R$_4$-X (XVIII) to give the compound having the structure of formula (I) or formula (II), wherein
R$_4$ is the formula (III), formula (IV), formula (V) or formula (VI), (III)

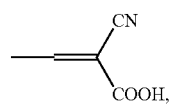

(IV)

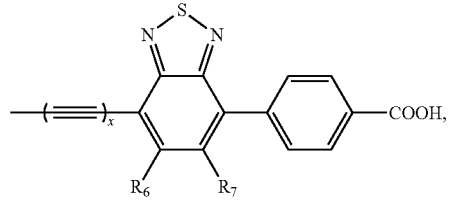

(V)

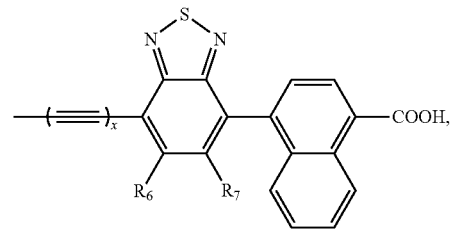

(VI)

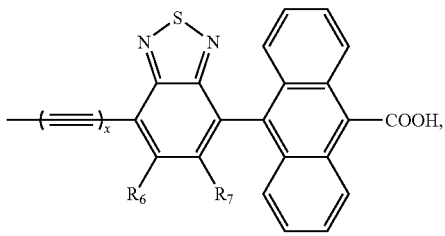

wherein R$_6$ and R$_7$ are independently selected from H, F, C$_1$-C$_{36}$ alkyl, phenyl substituted with C$_1$-C$_{36}$ alkyl, and phenyl substituted with C$_1$-C$_{36}$ alkoxy; and x is 0 or 1; and X is H, Br or I.

9. The process according to claim 8, wherein said step 2-1) is performed as follows:

2-1-1) converting the compound having the structure of formula (XV) into a compound having the structure of formula (XIX):

(XIX)

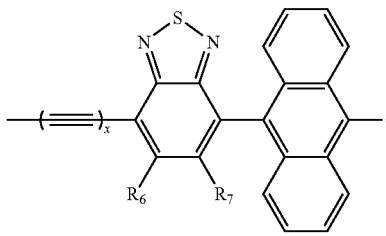

wherein
R$_1$ is C$_1$-C$_{36}$ alkyl;
R$_2$ and R$_3$ are independently selected from H, C$_1$-C$_{36}$ alkyl, phenyl substituted with C$_1$-C$_{36}$ alkyl, and phenyl substituted with C$_1$-C$_{36}$ alkoxy; and
R$_5$ is H, aryl or C$_1$-C$_{36}$ alkyl; and 2-1-2) converting the compound having the structure of formula (XIX) into the compound having the structure of formula (XVI) or formula (XVII).

10. A dye-sensitized solar cell comprising an organic dye layer, wherein the organic dye layer contains the organic dye according to claim 1.

* * * * *